United States Patent
Remmereit et al.

(10) Patent No.: US 11,628,152 B2
(45) Date of Patent: *Apr. 18, 2023

(54) LIPID COMPOSITIONS CONTAINING BIOACTIVE FATTY ACIDS

(71) Applicant: Sciadonics, Inc., Long Lake, MN (US)

(72) Inventors: Jan Remmereit, Hovdebygda (NO); Alvin Berger, Long Lake, MN (US)

(73) Assignee: Sciadonics, Inc., Long Lake, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/233,809

(22) Filed: Apr. 19, 2021

(65) Prior Publication Data

US 2021/0308088 A1 Oct. 7, 2021

Related U.S. Application Data

(63) Continuation of application No. 16/747,693, filed on Jan. 21, 2020, now Pat. No. 10,980,763, which is a continuation of application No. 16/222,320, filed on Dec. 17, 2018, now Pat. No. 10,537,542, which is a continuation of application No. 14/774,432, filed as application No. PCT/US2014/022553 on Mar. 10, 2014, now Pat. No. 10,154,979.

(60) Provisional application No. 61/775,836, filed on Mar. 11, 2013.

(51) Int. Cl.

| | |
|---|---|
| *A61K 31/202* | (2006.01) |
| *A23D 9/007* | (2006.01) |
| *A23D 9/013* | (2006.01) |
| *A23L 33/12* | (2016.01) |
| *A61K 31/19* | (2006.01) |
| *A61K 31/201* | (2006.01) |
| *A23K 20/158* | (2016.01) |
| *A61L 27/12* | (2006.01) |
| *A61L 27/32* | (2006.01) |
| *A61L 27/42* | (2006.01) |
| *A61L 27/58* | (2006.01) |
| *A61K 9/00* | (2006.01) |
| *A61L 24/00* | (2006.01) |
| *A61L 27/36* | (2006.01) |
| *A61L 27/50* | (2006.01) |

(52) U.S. Cl.
CPC ............ *A61K 31/202* (2013.01); *A23D 9/007* (2013.01); *A23D 9/013* (2013.01); *A23K 20/158* (2016.05); *A23L 33/12* (2016.08); *A61K 9/0053* (2013.01); *A61K 31/19* (2013.01); *A61K 31/201* (2013.01); *A61L 27/12* (2013.01); *A61L 27/32* (2013.01); *A61L 27/425* (2013.01); *A61L 27/58* (2013.01); *A23V 2002/00* (2013.01); *A61L 24/0063* (2013.01); *A61L 27/3608* (2013.01); *A61L 27/50* (2013.01); *A61L 2400/12* (2013.01); *A61L 2400/18* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,456,912 A | 10/1995 | German et al. | |
| 6,034,132 A | 3/2000 | Remmereit | |
| 6,280,755 B1 | 8/2001 | Berger et al. | |
| 10,154,979 B2* | 12/2018 | Remmereit | ............ A23D 9/013 |
| 10,537,542 B2* | 1/2020 | Remmereit | .......... A61K 31/202 |
| 10,980,763 B2* | 4/2021 | Remmereit | ............... A61P 3/10 |
| 2012/0156171 A1 | 6/2012 | Breton et al. | |

FOREIGN PATENT DOCUMENTS

| | | | |
|---|---|---|---|
| EP | 1685834 | 8/2006 | |
| FR | 2756465 | 6/1998 | |
| JP | 61058536 | 3/1986 | |
| WO | WO 95/17897 | 7/1995 | |
| WO | WO-9517897 A1 * | 7/1995 | ............ A61K 31/20 |
| WO | WO 96/005164 | 2/1996 | |
| WO | WO 2006/009464 | 1/2006 | |

OTHER PUBLICATIONS

Barnathan et al. "Non-methylene-interrupted fatty acids from marine invertebrates: Occurrence, characterization and biological properties" Biochimie, vol. 91, No. 6, 2009, pp. 671-678.
Evans et al., "Total synthesis and spectral characterization of 5,8, 14-icosatrienoic acid and 5, 11, 14-icosatrienoic acid and their acetylenic analogues." Chem. Phys. Lipids, 38(4), 327-342, 1995.
International Search Report and Written Opinion, International Patent Application No. PCT/US2014/022553, dated May 6, 2014.

(Continued)

*Primary Examiner* — Melissa S Mercier
(74) *Attorney, Agent, or Firm* — Casimir Jones S.C.; J. Mitchell Jones

(57) ABSTRACT

Provided herein is technology relating to lipid compositions containing bioactive fatty acids and particularly, but not exclusively, to compositions and methods related to the production and use of structured lipid compositions containing sciadonic and/or pinoleic acid alone or in combination with other bioactive fatty acids including, but not limited to, eicosapentaenoic acid, docosahexaenoic acid, conjugated linoleic acid, and non-β-oxidizable fatty acid analogues such as tetradecylthioacetic acid.

9 Claims, No Drawings

(56) References Cited

OTHER PUBLICATIONS

Kennedy et al. "Influence of dietary conjugated linoleic acid (CLA) and tetradecylthioacetic acid (TTA) on growth, lipid composition and key enzymes of fatty acid oxidation in liver and muscle of Atlantic cod (*Gadus morhua* L.)" Aquaculture, vol. 264, No. 1-4, 2007, pp. 372-382.

Mohamed Vall Ould El Kebir et al. "Fatty Acids in Liver, Muscle and Gonad of three Tropical Rays including Non-Methylene-Interrupted Dienoic Fatty Acids" Lipids, vol. 42, No. 6, 2007, pp. 525-535.

Oikawa et al. Modification of skin coposition by conjugated linoleic acid alone or with combination of other fatty acids in mice, Br J Nutr, Aug. 2005;94(2):275-81. (Year:2005).

Smith et al. *Caltha palustris* L. Seed oil. A Sour of Four Fatty Acids with cis-5-unsaturate; Lipids, vol. 3, No. 1, Sep. 7, 1967.

\* cited by examiner

LIPID COMPOSITIONS CONTAINING BIOACTIVE FATTY ACIDS

CROSS-REFERENCE TO RELATED APPLICATIONS

This application is a continuation of U.S. patent application Ser. No. 16/747,693, filed Jan. 21, 2020, allowed as U.S. Pat. No. 10,980,763, which is a continuation of U.S. patent application Ser. No. 16/222,320, filed Dec. 17, 2018, allowed as U.S. Pat. No. 10,537,542, which is a continuation of U.S. patent application Ser. No. 14/774,432, filed Sep. 10, 2015, allowed as U.S. Pat. No. 10,154,979, which is a 371 U.S. National Phase Entry of International Application No. PCT/US2014/022553, filed Mar. 10, 2014, which claims priority to U.S. Provisional Patent Application No. 61/775,836, filed Mar. 11, 2013, the contents of which are incorporated by reference in their entireties.

FIELD OF TECHNOLOGY

Provided herein is technology relating to lipid compositions containing bioactive fatty acids and particularly, but not exclusively, to compositions and methods related to the production and use of structured lipid compositions containing sciadonic and/or pinoleic acid alone or in combination with other bioactive fatty acids including, but not limited to, eicosapentaenoic acid, docosahexaenoic acid, conjugated linoleic acid, and non-β-oxidizable fatty acid analogues such as tetradecylthioacetic acid.

BACKGROUND

Bioactive fatty acids have been implicated for the treatment of various diseases and conditions. Bioactive fatty acids from natural sources have formed the basis for many popular and successful dietary supplements including various fish oils.

A number of bioactive fatty acids from a variety of sources have been identified including sciadonic acid, pinolenic acid, eicosapentaenoic acid, docosahexaenoic acid, and conjugated linoleic acid, just to name a few. Additionally, non-β-oxidizable fatty acid analogues such as tetradecylthioacetic acid have been shown to have excellent bioactivity. However, the efficacy of bioactive fatty acids in treating various diseases and conditions has been disputed.

What is needed in the art are improved compounds, compositions and formulations that enhance the usefulness of bioactive fatty acid for treating particular diseases and conditions.

SUMMARY

Provided herein is technology relating to lipid compositions containing bioactive fatty acids and particularly, but not exclusively, to compositions and methods related to the production and use of structured lipid compositions containing sciadonic and/or pinoleic acid alone or in combination with other bioactive fatty acids including, but not limited to, eicosapentaenoic acid, docosahexaenoic acid, conjugated linoleic acid, and non-β-oxidizable fatty acid analogues such as tetradecylthioacetic acid.

In some embodiments, the present invention provides a bioactive lipid composition comprising:
a first lipid component comprising at least one non-methylene-interrupted fatty acid moiety and a second lipid component comprising at least one bioactive fatty acid moiety selected from the group consisting of an omega-3 fatty acid moiety, a non-beta-oxidizable fatty acid moiety, and a conjugated linoleic acid moiety wherein the bioactive composition comprises at least 1% of the first lipid component w/w and at least 1% of the second lipid component w/w.

In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof.

In some embodiments, the at least one non-methylene-interrupted fatty acid moiety is selected from the group consisting free fatty acids, acylglycerides, phospholipids and esters comprising the at least one non-methylene-interrupted fatty acid moiety. In some embodiments, the at least one omega-3 fatty acid moiety is selected from the group consisting free fatty acids, acylglycerides, phospholipids and esters comprising the at least one omega-3 fatty acid moiety. In some embodiments, the at least one non-beta-oxidizable fatty acid moiety is selected from the group consisting free fatty acids, acylglycerides, phospholipids and esters comprising the at least one non-beta-oxidizable fatty acid moiety. In some embodiments, the at least one conjugated linoleic acid moiety is selected from the group consisting free fatty acids, acylglycerides, phospholipids and esters comprising the at least one conjugated linoleic acid moiety.

In some embodiments, the composition comprises at least 5%, 10%, 20%, 30%, 40%, 50%, 60%, 70%, 80%, 90%, 95%, or 99% w/w of the first lipid component. In some embodiments, the composition comprises at least 5%, 10%, 20%, 30%, 40%, 50%, 60%, 70%, 80%, 90%, 95%, or 99% w/w of the second lipid component.

In some embodiments, the compositions of the present invention comprise defined ratios of bioactive fatty acids. The bioactive fatty acids are preferably provided in the compositions as free fatty acids or as derivatives comprising a fatty acid moiety such as fatty acid esters (e.g., ethyl esters), acylglycerides (e.g., triglycerides), or phospholipids. The ratios refer to the weight ratios of the bioactive fatty acids in the compositions. Accordingly, in some embodiments, the compositions comprise a ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a ratio of non-methylene-interrupted fatty acid:one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a ratio of non-methylene-interrupted fatty acid:one or more other bioactive fatty acids of from 1:50 to 1:3, from 1:20 to 1:3, from 1:10 to 1:3, from 1:5 to 1:3, or from 1:4 to 1:3. In some embodiments, the compositions comprise a ratio of non-methylene-interrupted fatty acid:one or more other bioactive fatty acids of from 1:50 to 1:5, from 1:20 to 1:5, or from 1:10 to 1:5. In some embodiments, the compositions comprise a ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a ratio of one or more bioactive fatty acids that are not a non-methylene-interrupted fatty acid:non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a ratio of one or more bioactive fatty acids that are not a non-methylene-interrupted fatty acid:non-methylene-interrupted fatty acid of from 1:50 to 1:5, from 1:20 to 1:5, or from 1:10 to 1:5. In some embodiments, the compositions comprise a ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA. In some embodiments, the composition further comprise at least one pharmaceutically acceptable carrier. In some embodiments, the composition comprises an oil, powder, crystal, wax, emulsion, micelle, vesicle, or film.

In some embodiments, the present invention provides an oral delivery vehicle, food product, nutritional supplement, dietary supplement or function food comprising the bioactive lipid composition of described above.

In some embodiments, the present invention provides a structured phospholipid composition comprising phospholipid molecules of the following structure:

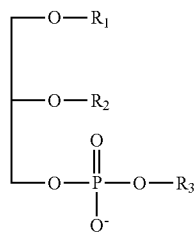

wherein R1 and R2 are fatty acid moieties or —H and R3 is —H or a phospholipid head group such that the composition comprises at least 1% w/w of at least one non-methylene-interrupted fatty acid moiety and at least 1% w/w of a second bioactive lipid moiety.

In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the second bioactive lipid moiety is selected from the group consisting of an omega-3 fatty acid moiety, a non-beta-oxidizable fatty acid moiety, a conjugated linoleic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof. In some embodiments, the composition comprises at least 5%, 10%, 20%, 30%, 40%, 50%, 60%, 70%, 80%, 90%, 95%, or 99% w/w of the at least one non-methylene-interrupted fatty acid moiety. In some embodiments, the composition comprises at least 5%, 10%, 20%, 30%, 40%, 50%, 60%, 70%, 80%, 90%, 95%, or 99% of the second bioactive lipid moiety.

In some embodiments, the phospholipids comprise a weight ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a weight ratio of non-methylene-interrupted fatty acid:one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of non-methylene-interrupted fatty acid:one or more other bioactive fatty acids of from 1:50 to 1:3, from 1:20 to 1:3, from 1:10 to 1:3, from 1:5 to 1:3, or from 1:4 to 1:3. In some embodiments, the compositions comprise a weight ratio of non-methylene-interrupted fatty acid:one or more other bioactive fatty acids of from 1:50 to 1:5, from 1:20 to 1:5, or from 1:10 to 1:5. In some embodiments, the compositions comprise a weight ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a weight ratio of one or more bioactive fatty acids that are not a non-methylene-interrupted fatty acid: non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a weight ratio of one or more bioactive fatty acids that are not a non-methylene-interrupted fatty acid:nonmethylene-interrupted fatty acid of from 1:50 to 1:5, from 1:20 to 1:5, or from 1:10 to 1:5. In some embodiments, the compositions comprise a weight ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA.

In some embodiments, the compositions further comprise at least one pharmaceutically acceptable carrier. In some embodiments, the composition comprises an oil, powder, crystal, wax, emulsion, micelle, vesicle, or film.

In some embodiments, the present invention provides an oral delivery vehicle, food product, nutritional supplement, dietary supplement or function food comprising the structured phospholipid composition described above.

In some embodiments, the present invention provides a structured acylglycerol composition comprising acylglycerol molecules of the following structure:

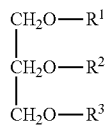

wherein R1, R2 and R3 are fatty acid moieties or —H such that the composition comprises at least 1% w/w of at least one non-methylene-interrupted fatty acid moiety and at least 1% w/w of a second bioactive lipid moiety. In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the second bioactive lipid moiety is selected from the group consisting of an omega-3 fatty acid moiety, a non-beta-oxidizable fatty acid moiety, a conjugated linoleic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof. In some embodiments, the composition comprises at least 5%, 10%, 20%, 30%, 40%, 50%, 60%, 70%, 80%, 90%, 95%, or 99% w/w of the at least one non-methylene-interrupted fatty acid moiety. In some embodiments, the composition comprises at least 5%, 10%, 20%, 30%, 40%, 50%, 60%, 70%, 80%, 90%, 95%, or 99% of the second bioactive lipid moiety.

In some embodiments, the acylglycerols, preferably triglycerides, comprise a weight ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a weight ratio of non-methylene-interrupted fatty acid:one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of non-methylene-interrupted fatty acid:one or more other bioactive fatty acids of from 1:50 to 1:3, from 1:20 to 1:3, from 1:10 to 1:3, from 1:5 to 1:3, or from 1:4 to 1:3. In some embodiments, the compositions comprise a weight ratio of non-methylene-interrupted fatty acid:one or more other bioactive fatty acids of from 1:50 to 1:5, from 1:20 to 1:5, or from 1:10 to 1:5. In some embodiments, the compositions comprise a weight ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a weight ratio of one or more bioactive fatty acids that are not a non-methylene-interrupted fatty acid:non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a weight ratio of one or more bioactive fatty acids that are not a non-methylene-interrupted fatty acid:non-methylene-interrupted fatty acid of from 1:50 to 1:5, from 1:20 to 1:5, or from 1:10 to 1:5. In some embodiments, the compositions comprise a weight ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA.

In some embodiments, the compositions further comprise at least one pharmaceutically acceptable carrier. In some embodiments, the composition comprises an oil, powder, crystal, wax, emulsion, micelle, vesicle, or film.

In some embodiments, the present invention provides an oral delivery vehicle, food product, nutritional supplement, dietary supplement or function food comprising the structured acylglycerol composition described above.

In some embodiments, the present invention provides a bioactive lipid composition comprising at 1% w/w of the structured phospholipid composition as described above and at least 1% w/w of the structured acylglyceride composition as described above.

In some embodiments, the present invention provides a method of treating a subject comprising administering to the subject the bioactive lipid composition, structured phospholipid composition or structured acylglyceride composition or oral delivery vehicle, food product, nutritional supplement, dietary supplement or function food as described above to a subject in need thereof. In some embodiments, the administration or oral, topical, parenteral, enteral, transdermal, intradermal, intraocular, intravitreal, sublingual, or intravaginal.

In some embodiments, the present invention provides a method of reducing obesity, inducing weight loss, increasing lean body mass, increasing muscularity, increasing muscle mass, improving body composition, alleviating one or more symptoms metabolic syndrome, treating diabetes, decreasing insulin resistance, reducing inflammation, improving concentration, memory, cognitive function, attention and treating, alleviating or improving one or more of the following diseases or conditions: restenosis, arteriosclerosis, coronary heart disease, thrombosis, myocardial infarction, stroke, hypertension, fatty liver, diabetes, hyperglycaemia, hyperinsulinemia, and stenosis, rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation, comprising: administering to a subject in need thereof the bioactive lipid composition, structured phospholipid composition or structured acylglyceride composition or oral delivery vehicle, food product, nutritional supplement, dietary supplement or function food of any of claims 1 to 9. In some embodiments, the administration or oral, topical, parenteral, enteral, transdermal, intradermal, intraocular, intravitreal, sublingual, or intravaginal.

In some embodiments, the present invention provides a method of treating diabetes, ameliorating the symptoms of diabetes, providing nutritional support to a subject with diabetes, promoting healthy blood sugar levels, supporting efficient insulin production and secretion, and supporting healthy glucose metabolism, comprising: administering to a subject in need thereof the bioactive lipid composition, structured phospholipid composition or structured acylglyceride composition or oral delivery vehicle, food product, nutritional supplement, dietary supplement or function food as described above. In some embodiments, the administration or oral, topical, parenteral, enteral, transdermal, intradermal, intraocular, intravitreal, sublingual, or intravaginal.

Additional embodiments will be apparent to persons skilled in the relevant art based on the teachings contained herein.

DETAILED DESCRIPTION

Provided herein is technology relating to lipid compositions containing bioactive fatty acids and particularly, but not exclusively, to compositions and methods related to the production and use of structured lipid compositions containing sciadonic and/or pinoleic acid alone or in combination with other bioactive fatty acids including, but not limited to, eicosapentaenoic acid, docosahexaenoic acid, conjugated linoleic acid, and non-β-oxidizable fatty acid analogues such as tetradecylthioacetic acid.

This technology is described below, wherein the section headings are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, "feeding" refers to providing a substance, compound, composition, etc. to a living organism. For example, the substance, compound, composition, etc. may be an energy source, a carbon source, a nutrient, or a source of other elements, molecules, and/or precursors of biological molecules that are used by the living organism and/or are metabolized (e.g., catabolized, anabolized) by the living organism. The substance, compound, composition, etc. is not necessarily a substance, compound, composition, etc. that the living organism encounters in its native milieu, but may be a synthetic substance, compound, composition, etc. or a natural substance, compound, composition, etc. that is nevertheless used by the living organism for metabolism. The substance, compound, composition, etc. may be added to a culture medium or a substrate in which or on which the living organism lives and/or grows.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance).

As used herein, the term "individual" refers to vertebrates, particularly members of the mammalian species. The term includes but is not limited to domestic animals, sports animals, primates, and humans.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoralkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

As used herein, the term "heterocycle" refers to a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula —OR, where R is an alkyl group. By "aryloxy" is meant a chemical substituent of the formula —OR', where R' is an aryl group.

As used herein, the term "$C_{x-y}$ alkaryl" refers to a chemical substituent of formula —RR', where R is an alkyl group of x to y carbons and R' is an aryl group as defined elsewhere herein.

As used herein, the term "$C_{x-y}$ alkheteraryl" refers to a chemical substituent of formula RR", where R is an alkyl group of x to y carbons and R" is a heteroaryl group as defined elsewhere herein.

As used herein, the term "halide" or "halogen" or "halo" refers to bromine, chlorine, iodine, or fluorine.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

For structural representations where the chirality of a carbon has been left unspecified it is to be presumed by one skilled in the art that either chiral form of that stereocenter is possible.

EMBODIMENTS OF THE TECHNOLOGY

Provided herein is technology relating to lipid compositions containing bioactive fatty acids and particularly, but not exclusively, to compositions and methods related to the production and use of structured lipid compositions containing sciadonic and/or pinoleic acid alone or in combination with other bioactive fatty acids including, but not limited to, eicosapentaenoic acid, docosahexaenoic acid, conjugated linoleic acid, and non-β-oxidizable fatty acid analogues such as tetradecylthioacetic acid. Below, sources of bioactive fatty acids, lipid compositions comprising bioactive fatty acids, methods for making the compositions and uses of the compositions are described.

Non-Methylene-Interrupted Fatty Acids

The term non-methylene-interrupted fatty acid, the acronym for which is NMIFA, refers to a fatty acid with a series of double bonds in which at least one adjacent pair of double bonds is separated by at least two carbon atoms, i.e., by a group other than a single methylene group. Examples of NMIFA include, but are not limited to, 5,11,14-eicosatrienoic acid; 5,9,12-cis-octadecatrienoic acid; and 5,11,14,17-eicosatetraenoic acid. Preferred NMIFAs have the following formula, wherein the NMIFA is an acid, a salt or an ester, and R1 is a $C_1$-$C_5$ alkyl group and R2 is a $C_2$-$C_6$ alkyl group, may be advantageously used for the preparation of a composition intended to modulate the metabolism of lipids in superficial mammalian tissues.

Particularly preferred NMIFAs are those in which R1 is a $C_3$ alkyl group and R2 is a $C_2$-$C_6$ alkyl group, or in which R2 is a $C_4$ alkyl group and R1 is a $C_1$-$C_5$ alkyl group. The most preferred is that in which R1 is an n-propyl group and R2 is an n-butyl group (5,11,14-eicosatrienoic acid, also called 20:3(5,11,14)). The NMIFAs may be preferably provided as triglycerides, phospholipids, fatty acids ester, free fatty acids or combinations thereof.

Sciadonic acid (5,11,14-eicosatrienoic acid, 20:3Δ5,11,14) is a polyunsaturated fatty acid containing non-methylene-interrupted double bonds, such as a Δ5-ethylenic bond. Sciadonic acid is often found in gymnosperms, in seed oils, leaves, and wood. It is also found in a few angiosperms, especially in seed oils. Sciadonic acid has several biological activities, including lowering triglyceride and cholesterol levels, reducing reperfusion injury, modifying autoimmune response, having cannabimimetic effect, treatment of skin disease, and treatment of sensitive or dry skin. WO 95/17987 (The Regents of the University of California) shows that broad class of NMIFAs, including 5,11,14-eicosatrienoic acid, may be used in an effective amount for suppressing autoimmune diseases in general, for example rheumatoid arthritis, lupus erythmatosis, multiple sclerosis, myasthenia gravis, and about 30 other diseases currently known. NMIFAs, including 5,11,14-eicosatrienoic acid, are further described in U.S. Pat. Nos. 5,456,912 and 6,280,755 as well as US Publ. No. 20120156171, each of which is incorporated herein by reference in its entirety.

Pinolenic acid ((5Z,9Z,12Z)-octadeca-5,9,12-trienoic acid; all-cis-5,9,12-18:3) is a fatty acid contained in Siberian Pine nuts, Korean Pine nuts and the seeds of other pines (Pinus species). The highest percentage of pinolenic acid is found in Siberian pine nuts and the oil produced from them. JP 61 058 536 (Nippon Oil) discloses a method for purifying pine nut oil containing at least 10% by weight of 5,9,12-cis-octadecatrienoic acid which exhibits a curative effect against arterial hypertension.

WO 96 05 164 (Broadben Nominees Pty) discloses an anti-inflammatory preparation comprising a purified active fraction, for example 5,11,14,17-eicosatetraenoic acid, isolated from a lipid extract of Perna canalicullus or Mytilus edulis.

Some of the NMIFAs of the invention are naturally occurring substances. Others may be synthesized according to well-known published methodology (see for example Evans et al., Chem. Phys. Lipids, 38, 327-342, 1995).

For example, 20:3(5,11,14) is a naturally occurring substance which generally occurs as one fatty acid in a mixture of fatty acids. This NMIFA is found in a wide variety of plants as minor or major fraction of the total fatty acid composition. Both the extraction of the mixture of fatty acid from their natural sources and the extraction of the 20:3(5,11,14) from the resulting fatty acids can be achieved by conventional extraction and purification methods well known among those skilled in the art.

The natural sources of fatty acids containing 20:3(5,11,14) are primarily plant seeds, and prominent among these are conifers and ornamental shrubs. The seed oils from these plants are similar to normal edible oils, containing largely oleic, linoleic and linolenic acids, but also containing useful amounts of NMIFAs. Table 1 lists examples of seeds whose lipid contents contain significant amounts of 20:3(5,11,14).

| Source | % of 20:3 (5, 11, 14) among total fatty acids | Source | % of 20:3 (5, 11, 14) among total fatty acids |
|---|---|---|---|
| Juniperis virginiensis | 14.8 | Sciadopitys verticallata | 15 |
| Plarycladus orientalis | 3 | Caltha pulustris | 23 |
| Juniperis chinensis | 12.3 | Calitrus rhombaldea | 14 |
| Torreya nucifera | 7 | Mortierella alpina* | 7 |
| Podocarpus nagi | 24 | Ephedra campylopoda | 22 |
| Anemone rivularis | 10 | Anemone leveillel | 6 |
| Cimaifuga racemosa | 6 | Erantis hyemalis | 6 |
| Gingko biloba | 2.2 | Pinus silvestris | 7 |

*see the Japanese patent JP5276964 (Suntory LTD)

Purification of 20:3(5,11,14) may be in particular achieved by (1) choosing a starting seed source high in total fat content and 20:3(5,11,14) content but not containing other contaminating trienes, in particular alpha-linolenic acid (18:3n-3) and gamma-linolenic acid (18:3n-6) (*Podocarpus nagi*, Table 1, is such an example); (2) extracting the lipids with isopropanol and chloroform according to the method of Nichols (Biochim. Biophys Acta 70: 417, 1963); (3) conventional degumming and decoloring methods; (4) preparing methyl esters with 2% methanolic sulfuric acid according to the method of Christie (p. 52-53, in Lipid Analysis, Pergamon Press, Oxford, 1982); (5) eluting 20:3 (5,11,14) methyl ester from a silver nitrate impregnated acid-washed Florisil column with a hexane:ether mixture ranging from 9:1 to 8:2 (volume/volume) according to Carroll, J. Am. Oil Chem. Soc. 40: 413, 1963; Wilner, Chem. Ind (Lond) October, 30: 1839, 1965; Merck ChromNews 4(1): 1995; Anderson, J. Lipid Res. 6: 577, 1965; and Teshima, Bull. Jap. Soc. Scien. Fish. 44: 927, 1978); (6) removing contaminating silver ions by the method of Akesson (Eur. J. Biochem. 9:463, 1969); and (7) optionally converting the methyl ester back to the free acid form by saponification in 1 M potassium hydroxide in 95% ethanol according to Christie (p. 51-52, in Lipid Analysis, Pergamon Press, Oxford, 1982).

Omega-3 Fatty Acids

Omega 3 fatty acids (also called ω-3 fatty acids or n-3 fatty acids are fats commonly found in marine and plant oils. They are polyunsaturated fatty acids with a double bond (C=C) starting after the third carbon atom from the end of the carbon chain. The fatty acids have two ends—the acid (COOH) end and the methyl (CH3) end. The location of the first double bond is counted from the methyl end, which is also known as the omega (ω) end or the n end.

Examples of N-3 fatty acids that are important in human physiology are α-linolenic acid (18:3, n-3; ALA), eicosapentaenoic acid (20:5, n-3; EPA), and docosahexaenoic acid (22:6, n-3; DHA). These three polyunsaturates have either 3, 5, or 6 double bonds in a carbon chain of 18, 20, or 22 carbon atoms, respectively. As with most naturally-produced fatty acids, all double bonds are in the cis-configuration, in other words, the two hydrogen atoms are on the same side of the double bond; and the double bonds are methylene interrupted, i.e., there are two single bonds between each pair of adjacent double bonds. Other N-3 fatty acids useful in the present invention include:

Hexadecatrienoic acid (HTA); 16:3 (n-3); all-cis-7,10,13-hexadecatrienoic acid

α-Linolenic acid (ALA); 18:3 (n-3); all-cis-9,12,15-octadecatrienoic acid

Stearidonic acid (SDA); 18:4 (n-3); all-cis-6,9,12,15-octadecatetraenoic acid

Eicosatrienoic acid (ETE); 20:3 (n-3); all-cis-11,14,17-eicosatrienoic acid

Eicosatetraenoic acid (ETA); 20:4 (n-3); all-cis-8,11,14,17-eicosatetraenoic acid Eicosapentaenoic acid (EPA); 20:5 (n-3); all-cis-5,8,11,14,17-eicosapentaenoic acid Heneicosapentaenoic acid (HPA); 21:5 (n-3; all-cis-6,9,12,15,18-heneicosapentaenoic acid Docosapentaenoic acid (DPA); 22:5 (n-3); all-cis-7,10,13,16,19-docosapentaenoic acid Docosahexaenoic acid (DHA); 22:6 (n-3); all-cis-4,7,10,13,16,19-docosahexaenoic acid Tetracosapentaenoic acid; 24:5 (n-3); all-cis-9,12,15,18,21-tetracosapentaenoic acid Tetracosahexaenoic acid (Nisinic acid); 24:6 (n-3); all-cis-6,9,12,15,18,21-tetracosahexaenoic acid In preferred embodiments, the omega-3 fatty acids are marine omega-3 fatty acids such as EPA, DHA or DPA. Sources of these fatty acids include, but are not limited to, fish oils (herring oil, salmon oil, tuna oil, anchovy oil, mackerel oil, cod liver oil, sardine oil, and the like), krill oil, Calanus oil, seal oil, algal oils, bacterial oils, green lipped mussels oil, and the like. Plants may also be genetically modified to produce marine omega-3 fatty acids. The marine omega-3 fatty acids may be preferably provided as triglycerides, phospholipids or fatty acids esters or combinations thereof. Herring oil and krill oil are especially preferred sources of marine oil phospholipids. The technology for producing omega-3 concentrates via esterification of marine fatty acids and up-concentration by distillation is well known in the art.

Conjugated Linoleic Acid

In some embodiments, the lipid compositions of the present invention comprise one or more conjugated linoleic acid moieties. The conjugated linoleic acid moieties may be preferably provided as free fatty acids, esters, acylglycerides or phospholipids. Preferably conjugated linoleic acid isomers include, but are not limited to c9,t11 CLA, t10,c12 CLA, t9,t11 CLA and t10,t12 CLA and combinations thereof. Methods for making CLA are described in detail in U.S. Pat. Nos. 8,207,225 7,966,056 7,776,353 7,514,096 7,452,548 7,115,759 7,094,420 7,078,051 7,029,691 6,891,054 6,677,470 6,610,868 6,524,527 6,410,761 6,380,409 6,333,353 6,225,486, each or which is incorporated by reference herein in its entirety.

Non-β-Oxidizable Analogues

The compounds according to the technology may also (especially in combination with sciadonic acid) comprise non-β-oxidizable fatty acid analogues as represented by the formula

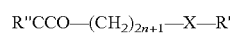

$$R''CCO-(CH_2)_{2n+1}-X-R'$$

wherein X is a sulfur atom, a selenium atom, an oxygen atom, a $CH_2$ group, a SO group, or a $SO_2$ group; n is an integer of 0 to 11; R' is a linear or branched alkyl group, saturated or unsaturated, optionally substituted, wherein the main chain of the R' contains from 13 to 23 carbon atoms and optionally one or more heterogroups selected from the group comprising an oxygen atom, a sulfur atom, a selenium atom, an oxygen atom, a $CH_2$ group, a SO group, and a $SO_2$ group; and R" is a hydrogen atom or an alkyl group containing from 1 to 4 carbon atoms. In some preferred embodiments, the non-β-oxidizable fatty acid analogue is tetradecylthioacetic acid (TTA), having the structure:

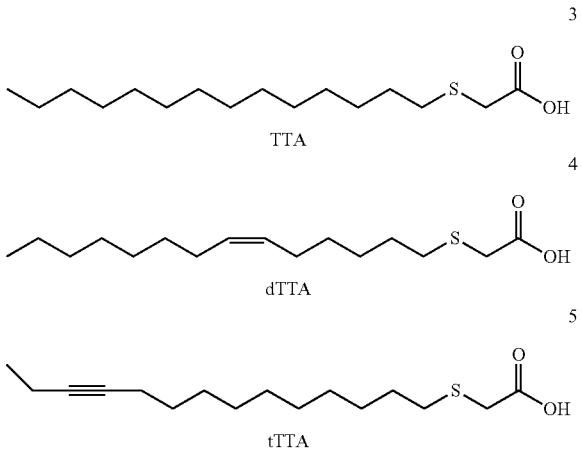

It is understood that analogues that contain one of Se, SO, $SO_2$, O, or $CH_2$ in place of sulfur also provide useful pharmaceutical activity. In addition, the length and degrees of saturation of the alkyl chains can also be varied.

The sulfur atom is more electronegative than carbon. Hence, the 3-thia acid is slightly more acidic than its corresponding fatty acid. Thia fatty acids are also more polar and slightly more soluble in water than fatty acids of corresponding chain length. Synthetic routes to TTA and molecules comprising TTA are provided in, e.g., U.S. Pat. Nos. 5,093,365; 6,046,237; 6,365,628; 6,417,232; 6,441,036; 7,026,356; 7,378,443; 7,902,399; 8,088,825; preparation of mono-, di-, and triglycerides and nitrogen comprising lipids according to the technology are disclosed in detail in U.S. Pat. No. 7,375,135; and the synthesis of phospholipids comprising TTA are provided in, e.g., 8,178,713.

Other Natural Lipids and/or Fatty Acids

While the structure and biological function of many of the major lipids from marine organisms have been studied, less is known of the properties of the structure and function of lipids present in marine organisms in small amounts. Microorganisms such as marine bacteria and algae are the primary source for lipids and/or lipid precursors in marine food chains Many potentially bioactive compounds are detectable in fish and other marine animals in low amounts, e.g., due to losses in the food chain. These bioactive lipids may be present in a larger amount in microorganisms nearer the base of the food chain. That is, it is contemplated that lipid extracts (e.g., oils, fractions, etc.) demonstrate high specific biological activities as isolated from microorganisms.

For example, furan fatty acids have biological activities such as scavenging free radicals (e.g., by reacting readily with peroxyl radicals to generate dioxoenes) and thus may contribute to the protective properties of fish and fish oil diets relative to heart disease. Furan fatty acids are tri- or tetra-substituted furan derivatives comprising either a $C_3$ or $C_5$ side chain in one of the alpha positions and a straight long-chain saturated acid with a carboxylate at its end in the other alpha position.

Furan fatty acids have been found in fish, algae, bacteria, and fungi, and are generated in large amounts by algae and in small to moderate amounts by plants and other microorganisms. Marine organisms (such as fish) and mammals obtain furan fatty acids in food and metabolize them into phospholipids. Furan fatty acids are catabolized to dibasic urofuran acids and excreted in the urine. Due to their molecular structure, furan fatty acids are contemplated to be catabolized more slowly than other lipids in mammals, and thus potentially to be bioactive in relation to energy metabolism.

As discussed elsewhere, unusual lipids (e.g., phytanyl ether lipids) are present in the Archaea, particularly in thermophiles and hyperthermophiles, some of which grow optimally at temperatures higher than 80° C. In addition, unusual lipids have been found in some thermophilic members of the Bacteria. For example, the lipids found in *Thermotoga* spp. (e.g., *T. maritima*) comprise a mixture of ether lipids and ester lipids, mainly polar. Liposomes produced from these lipids demonstrate high stability at high and low temperatures, are resistant to acids and bases, and are resistant to high pressure. In addition, these lipids affect membrane properties and thus may result in altered absorption and permeability of nutrients.

Bioactive Lipid Compositions

The present invention provides bioactive lipid compositions comprising one or more bioactive fatty acid moieties, and in particularly preferred embodiments NMIFAs, alone or in combination with other bioactive fatty acid moieties. The bioactive lipid compositions are preferable characterized by comprising a particular weight/weight (w/w) percentage of the bioactive fatty acids which refers to the weight of the specific fatty acid or fatty acid moiety as a percentage of the total weight of the composition. The bioactive lipid compositions of the present invention may comprise free fatty acids, fatty acid esters, monoglycerides, diglycerides, triglycerides, phospholipids and combinations thereof. Where the bioactive fatty acid is attached to an alkyl group, glyceride molecule, or phosphoglyceride molecule via an ester or ether bond the fatty acid portion of the molecule is referred to as a fatty acid moiety and the weight percentage of the fatty acid moiety in the composition is expressed as the weight of the particular fatty acid moiety as a percentage of the total weight of the composition.

Thus, the compositions according to the present technology are either fatty acids analogous to naturally occurring fatty acids, especially NMIFAs alone in combination with other bioactive fatty acids, or naturally occurring lipids comprising said fatty acid analogues. In vivo, the fatty acid analogues show a strong preference for being incorporated into phospholipids. Incorporating fatty acid analogues in naturally occurring lipids (e.g., monoglycerides, diglycerides, triglycerides, and/or phospholipids) produces a compound with different absorption characteristics compared to the fatty acids. In addition, it is contemplated that incorporating fatty acid analogues in naturally occurring lipids (e.g., monoglycerides, diglycerides, triglycerides, and/or phospholipids) may also increase the bioavailability or stability.

For example, some embodiments of the technology relate to a triacylglycerol that includes a NMIFA alone in combination with other bioactive fatty acids. If such a triacylglycerol were taken orally, for instance in an animal food product, it would probably be transported like any triacylglycerol, e.g., from the small intestine in chylomicrons to the liver; then to the blood in lipoproteins to be stored in the adipose tissue or used by muscles, heart, or the liver; then by hydrolysis of the triacylglycerol into glycerol and three free fatty acids. The free fatty acids would at this point be the fatty acid analogue parent compound.

Embodiments also encompass glycerophospholipid derivatives of the NMIFA fatty acids, including, but not limited to, phosphatidylcholines, phosphatidylethanolamines, phosphatidylinositols, phosphatidylserines, and phosphatidylglycerols.

In some embodiments, the NMIFAs are incorporated into a sphingolipid derivative such as ceramide or a sphingomyelin. Like glycerophospholipids complexes, these compounds would be water insoluble and hydrophobic, and thus pass through biological membranes.

Additional embodiments include polar complexes such as, but not limited to, lysophospholipids, phosphatidic acids, alkoxy compounds, glycerocarbohydrates, gangliosides, and cerebrosides.

Accordingly, in some embodiments, the present invention provides bioactive lipid compositions comprising: a first lipid component comprising at least one non-methylene-interrupted fatty acid moiety and a second lipid component comprising at least one bioactive fatty acid moiety selected from the group consisting of an omega-3 fatty acid moiety, a non-beta-oxidizable fatty acid moiety, and a conjugated linoleic acid moiety. The first and second lipid components may preferably comprise free fatty acids, acylglycerides, phospholipids, esters and combinations thereof comprising the respective moiety. In some embodiments, the bioactive composition comprises at least 1% of said first lipid component w/w and at least 1% of said second lipid component w/w. In some embodiments, the composition comprises at least 1%, 2%, 3%, 4%, 5%, 10%, 20%, 30%, 40%, 50%, 60%, 70%, 80%, 90%, 95%, or 99% w/w of the first lipid component and at least 1%, 2%, 3%, 4%, 5%, 10%, 20%, 30%, 40%, 50%, 60%, 70%, 80%, 90%, 95%, or 99% w/w of the second lipid component such that the first and second lipid components do not exceed 100% of the composition. In some embodiments, the compositions comprise at least a third lipid component, an additional active component, or a carrier such as a pharmaceutically acceptable carrier. In these instances the compositions preferably comprise at least 1%, 2%, 3%, 4%, 5%, 10%, 20%, 30%, 40%, 50%, 60%, 70%, 80%, 90%, 95%, or 99% w/w of the first lipid component and at least 1%, 2%, 3%, 4%, 5%, 10%, 20%, 30%, 40%, 50%, 60%, 70%, 80%, 90%, 95%, or 99% w/w of the second lipid component such that the total amounts of the first and second lipid components and at least a third lipid component, additional active component and/or carrier do not exceed 100% of the composition. In some embodiments, the compositions comprise a weight ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a weight ratio of non-methylene-interrupted fatty acid:one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of non-methylene-interrupted fatty acid:one or more other bioactive fatty acids of from 1:50 to 1:3, from 1:20 to 1:3, from 1:10 to 1:3, from 1:5 to 1:3, or from 1:4 to 1:3. In some embodiments, the compositions comprise a weight ratio of non-methylene-interrupted fatty acid:one or more other bioactive fatty acids of from 1:50 to 1:5, from 1:20 to 1:5, or from 1:10 to 1:5. In some embodiments, the compositions comprise a weight ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a weight ratio of one or more bioactive fatty acids that are not a non-methylene-interrupted fatty acid:non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a weight ratio of one or more bioactive fatty acids that are not a non-methylene-interrupted fatty acid:non-methylene-interrupted fatty acid of from 1:50 to 1:5, from 1:20 to 1:5, or from 1:10 to 1:5. In some embodiments, the compositions comprise a weight ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA.

In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof.

The bioactive lipid composition may be preferably provided as an oil, powder, crystal, wax, emulsion, micelle, vesicle, or film. The bioactive lipid composition may be preferably provided in an oral delivery vehicle, food product, nutritional supplement, dietary supplement or functional food.

In some embodiments, the present invention provides structured phospholipid compositions comprising phospholipid molecules of the following structure:

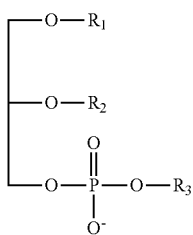

wherein R1 and R2 are fatty acid moieties or —H and R3 is —H or a phospholipid head group moiety such that the composition comprises at least 1% w/w of at least one non-methylene-interrupted fatty acid moiety and at least 1% w/w of a second bioactive lipid moiety. In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the bioactive lipid moiety is selected from the group consisting of an omega-3 fatty acid moiety, a non-beta-oxidizable fatty acid moiety, a conjugated linoleic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof. In some embodiments, the composition comprises at least 1%, 2%, 3%, 4%, 5%, 10%, 20%, 30%, 40%, 50%, 60%, 70%, 80%, 90%, 95%, or 99% w/w of the at least one non-methylene-interrupted fatty acid moiety and at least 1%, 2%, 3%, 4%, 5%, 10%, 20%, 30%, 40%, 50%, 60%, 70%, 80%, 90%, 95%, or 99% w/w of the second bioactive lipid moiety such that the total amounts of the respective non-methylene-interrupted fatty acid moiety and the second bioactive lipid moiety do not exceed 100% w/w of the composition. In some embodiments, the compositions comprise at least a third lipid component, an additional active component, or a carrier such as a pharmaceutically acceptable carrier. In some embodiments, the phospholipids comprise a weight ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a weight ratio of non-methylene-interrupted fatty acid:one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of non-methylene-interrupted fatty acid:one or more other bioactive fatty acids of from 1:50 to 1:3, from 1:20 to 1:3, from 1:10 to 1:3, from 1:5 to 1:3, from 1:4 to 1:3. In some embodiments, the compositions comprise a weight ratio of non-methylene-interrupted fatty acid:one or more other bioactive fatty acids of from 1:50 to 1:5, from 1:20 to 1:5, or from 1:10 to 1:5. In some embodiments, the compositions comprise a weight ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a weight ratio of one or more bioactive fatty acids that are not a non-methylene-interrupted fatty acid: non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a weight ratio of one or more bioactive fatty acids that are not a non-methylene-interrupted fatty acid:non-methylene-interrupted fatty acid of from 1:50 to 1:5, from 1:20 to 1:5, or from 1:10 to 1:5. In some embodiments, the compositions comprise a weight ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA.

Accordingly, articular embodiments relate to phospholipids comprising one or more of a non-methylene-interrupted fatty acid moiety and a second bioactive lipid moiety, for example, an omega-3 fatty acid moiety, a non-beta-oxidizable fatty acid moiety, and a conjugated linoleic acid moiety. Phospholipids according to the technology are not limited in the polar headgroup of the phospholipid. For example, the polar head group may be the polar head group of any suitable lipid.

In some embodiments, the phospholipid is a neutral or anionic phospholipid. For example, in some embodiments the polar head group is the polar head group of, or is derived from, a lipid such as a phospholipid, ceramide, triacylglycerol, lysophospholipid, phosphatidylserine, glycerol, alcohol, alkoxy compound, monoacylglycerol, ganglioside, sphingomyelin, cerebroside, phosphatidylcholine (e.g., dioleoylphosphatidylcholine (DOPC)), phosphatidylethanolamine (e.g., dioleoylphosphatidylethanolamine (DOPE)), phosphatidylinositol, diacylglycerol, phosphatidic acid, glycerocarbohydrate, polyalcohol, and/or phosphatidylglycerol.

Exemplary polar headgroups are, e.g.:
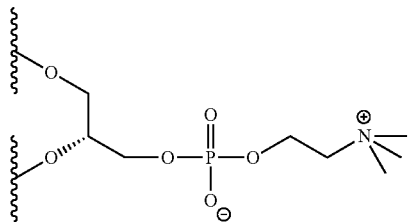
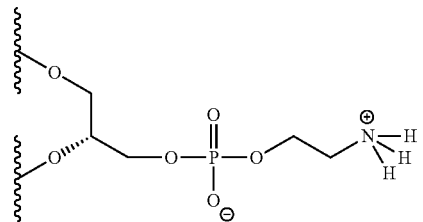
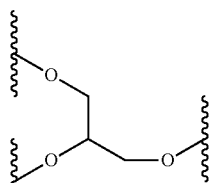
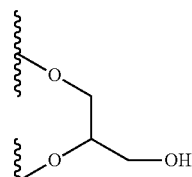
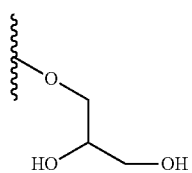
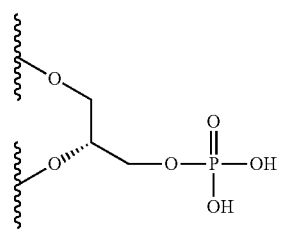
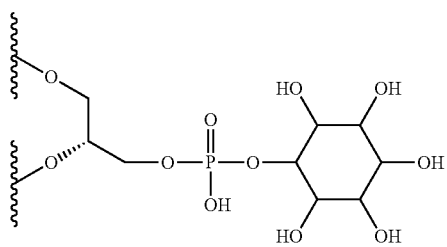
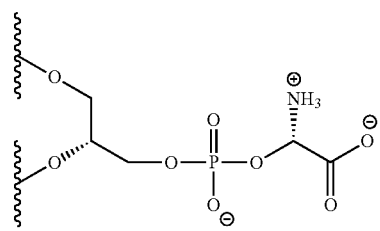
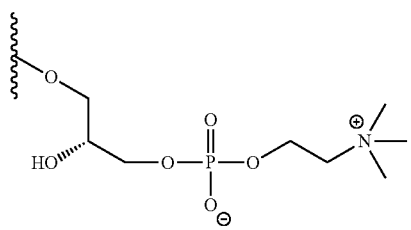
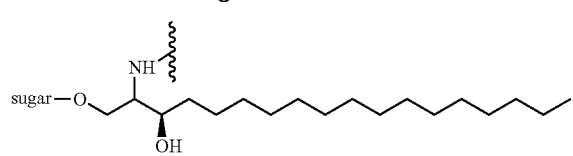
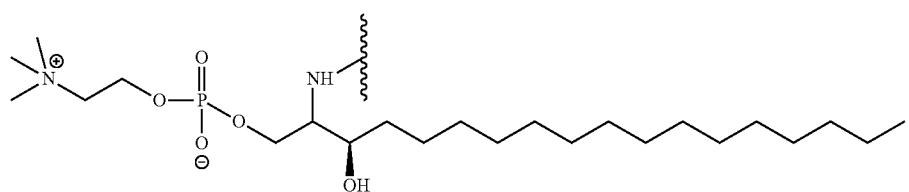

In some embodiments, the polar head group is, or is derived from, a triacylglycerol, e.g., having the structure

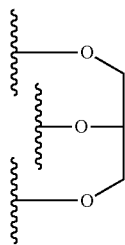

In some embodiments, the polar head group (PHG) comprises the group

—W-Linker-HG wherein W is selected from $CH_2$, O, $NR^1$, and S, wherein $R^1$ is H or a hydrocarbyl group, wherein Linker is an optional linker group, and HG is a head group.

The head group (HG) may be polar or non-polar. When HG is non-polar it may be rendered polar by group —C(O)W-Linker-. Such head groups are encompassed by the present definition provided —C(O)W-Linker-HG is polar and HG is polar when attached to the —C(O)W-Linker- group.

In some embodiments, the head group (HG) may be an alkyl group, e.g., having at least 5 carbons. In some embodiments, it is a $C_{5-100}$ alkyl group, a $C_{5-80}$ alkyl group, a $C_{5-60}$ alkyl group, a $C_{5-50}$ alkyl group, a $C_{5-40}$ alkyl group, $C_{5-30}$ alkyl group, or a $C_{5-20}$ alkyl group.

For example, in some embodiments the HG is the head group of, or is derived from, a lipid such as a phospholipid, ceramide, triacylglycerol, lysophospholipid, phosphatidylserine, glycerol, alcohol, alkoxy compound, monoacylglycerol, ganglioside, sphingomyelin, cerebroside, phosphatidylcholine, phosphatidylethanolamine, phosphatidylinositol, diacylglycerol, phosphatidic acid, glycerocarbohydrate, polyalcohol, and/or a phosphatidylglycerol.

Exemplary head groups are, e.g.:

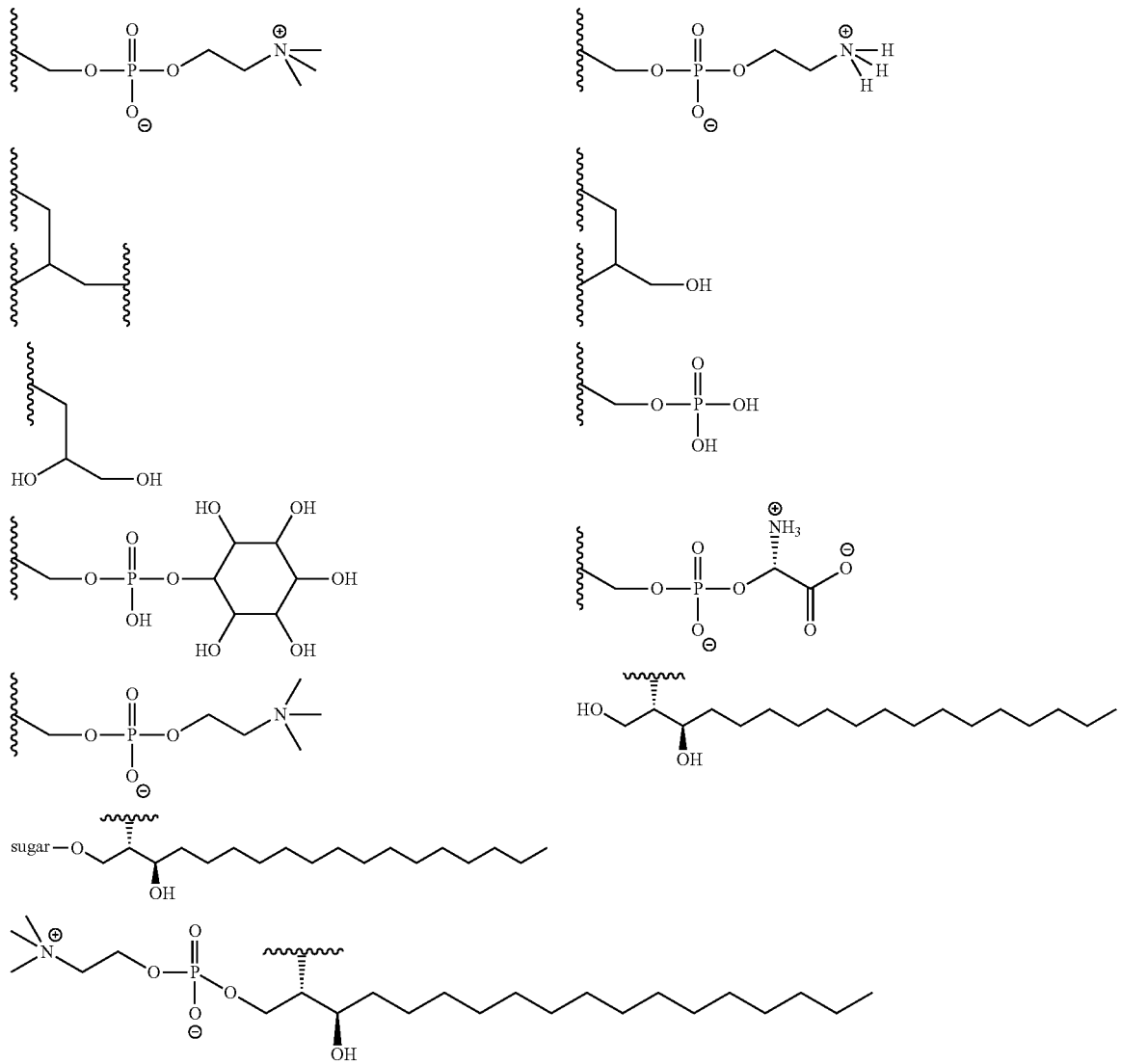

The structured phospholipid composition may be preferably provided as an oil, powder, crystal, wax, emulsion, micelle, vesicle, or film. The structured phospholipid composition may be preferably provided in an oral delivery vehicle, food product, nutritional supplement, dietary supplement or functional food.

In some embodiments, the present invention provides a structured acylglycerol composition comprising acylglycerol molecules of the following structure:

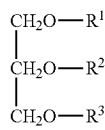

wherein R1, R2 and R3 are fatty acid moieties or —H such that said composition comprises at least 1% w/w of at least one non-methylene-interrupted fatty acid moiety and at least 1% w/w of a second bioactive lipid moiety. In some embodiments, the non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof. In some embodiments, the bioactive lipid moiety is selected from the group consisting of an omega-3 fatty acid moiety, a non-beta-oxidizable fatty acid moiety, a conjugated linoleic acid moiety and combinations thereof. In some embodiments, the omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof. In some embodiments, the non-beta-oxidizable fatty acid moiety is selected from the group consisting of a tetradecylthioacetic acid (TTA) moiety and a tetradecylselenoacetic acid (TSA) moiety and combinations thereof. In some embodiments, the conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof. In some embodiments, the composition comprises at least 1%, 2%, 3%, 4%, 5%, 10%, 20%, 30%, 40%, 50%, 60%, 70%, 80%, 90%, 95%, or 99% w/w of the at least one non-methylene-interrupted fatty acid moiety and at least 1%, 2%, 3%, 4%, 5%, 10%, 20%, 30%, 40%, 50%, 60%, 70%, 80%, 90%, 95%, or 99% of the second bioactive lipid moiety such that the total amounts of the respective non-methylene-interrupted fatty acid moiety and the second bioactive lipid moiety do not exceed 100% w/w of the composition. In some embodiments, the compositions comprise at least a third lipid component, an additional active component, or a carrier such as a pharmaceutically acceptable carrier. In some embodiments, the acylglycerols, preferably triglycerides, comprise a weight ratio of non-methylene-interrupted fatty acid:one or more other bioactive fatty acids of from 1:50 to 1:1, from 1:20 to 1:1, from 1:10 to 1:1, from 1:5 to 1:1, from 1:4 to 1:1, from 1:3 to 1:1, from 1:2 to 1:1, or from 1.5:1 to 1:1. In some embodiments, the compositions comprise a weight ratio of non-methylene-interrupted fatty acid: one or more other bioactive fatty acids of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of non-methylene-interrupted fatty acid:one or more other bioactive fatty acids of from 1:50 to 1:3, from 1:20 to 1:3, from 1:10 to 1:3, from 1:5 to 1:3, or from 1:4 to 1:3. In some embodiments, the compositions comprise a weight ratio of non-methylene-interrupted fatty acid:one or more other bioactive fatty acids of from 1:50 to 1:5, from 1:20 to 1:5, or from 1:10 to 1:5. In some embodiments, the compositions comprise a weight ratio of non-methylene-interrupted fatty acid:one or more other bioactive fatty acids of from 1:50 to 1:10, from 1:40 to 1:10, from 1:30 to 1:10, or from 1:20 to 1:10. In some embodiments, the compositions comprise a weight ratio of one or more bioactive fatty acids that are not a non-methylene-interrupted fatty acid:non-methylene-interrupted fatty acid of from 1:50 to 1:2, from 1:20 to 1:2, from 1:10 to 1:2, from 1:5 to 1:2, from 1:4 to 1:2, or from 1:3 to 1:2. In some embodiments, the compositions comprise a weight ratio of one or more bioactive fatty acids that are not a non-methylene-interrupted fatty acid:non-methylene-interrupted fatty acid of from 1:50 to 1:3, from 1:20 to 1:3, from 1:10 to 1:3, from 1:5 to 1:3, or from 1:4 to 1:3. In some embodiments, the compositions comprise a weight ratio of one or more bioactive fatty acids that are not a non-methylene-interrupted fatty acid:non-methylene-interrupted fatty acid of from 1:50 to 1:5, from 1:20 to 1:5, or from 1:10 to 1:5. In some embodiments, the compositions comprise a weight ratio of one or more bioactive fatty acids that are not a non-methylene-interrupted fatty acid:non-methylene-interrupted fatty acid of from 1:50 to 1:10, from 1:40 to 1:10, from 1:30 to 1:10, or from 1:20 to 1:10. In some embodiments, the one or more other bioactive fatty acid is one or more omega-3 fatty acids. In some embodiments, the omega-3 fatty acid is docosahexaenoic acid (DHA). In some embodiments, the omega-3 fatty acid is eicosapentaenoic acid (EPA). In some embodiments, the omega-3 fatty acid is docosapentaenoic acid (DPA). In some embodiments, the one or more omega-3 fatty acids are a combination of DHA and EPA. In some embodiments, the one or more bioactive fatty acids is conjugated linoleic acid. In some embodiments, the one or more bioactive fatty acids are a combination of CLA and one or more omega-3 fatty acids, preferably DHA and EPA. In some embodiments, the one or more bioactive fatty acids is a non-beta-oxidizable fatty acid, preferably tetradecylthioacetic acid (TTA). In some embodiments, the one or more bioactive fatty acids are a combination of a non-beta-oxidizable fatty acid, preferably TTA, and one or more omega-3 fatty acids, preferably DHA and EPA.

The structured acylglycerol composition may be preferably provided as an oil, powder, crystal, wax, emulsion, micelle, vesicle, or film. The structured phospholipid composition may be preferably provided in an oral delivery vehicle, food product, nutritional supplement, dietary supplement or functional food.

In some embodiments, the present invention provides bioactive lipid compositions comprising at least 1%, 2%, 3%, 4%, 5%, 10%, 20%, 30%, 40%, 50%, 60%, 70%, 80%, 90%, 95%, or 99% w/w of the structured phospholipid composition described above and at least at least 1%, 2%, 3%, 4%, 5%, 10%, 20%, 30%, 40%, 50%, 60%, 70%, 80%, 90%, 95%, or 99% w/w of the structured acylglycerol composition described above such that the total amount of the respective compositions does not exceed 100%.

The present invention likewise provides methods of using the compositions. These methods and uses are described in detail below but may be summarized as follows. In some embodiments, the present invention provides methods of treating a subject comprising administering to said subject the bioactive lipid composition, structured phospholipid composition or structured acylglyceride composition or oral delivery vehicle, food product, nutritional supplement, dietary supplement or function food as described above to a subject in need thereof. In some embodiments, the administration or oral, topical, parenteral, enteral, transdermal, intradermal, intraocular, intravitreal, sublingual, or intravaginal and may preferably comprise an effective amount of the composition.

In further preferred embodiments, the present invention provides methods of reducing obesity, inducing weight loss, increasing lean body mass, increasing muscularity, increasing muscle mass, improving body composition, alleviating one or more symptoms metabolic syndrome, treating diabetes, decreasing insulin resistance, reducing inflammation, improving concentration, memory, cognitive function, attention and treating, alleviating or improving one or more of the following diseases or conditions: re stenosis, arteriosclerosis, coronary heart disease, thrombosis, myocardial infarction, stroke, hypertension, fatty liver, diabetes, hyperglycaemia, hyperinsulinemia, and stenosis, rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation, comprising administering to a subject in need thereof the bioactive lipid composition, structured phospholipid composition or structured acylglyceride composition or oral delivery vehicle, food product, nutritional supplement, dietary supplement or function food as described above. In some embodiments, the administration or oral, topical, parenteral, enteral, transdermal, intradermal, intraocular, intravitreal, sublingual, or intravaginal and may preferably comprise an effective amount of the composition. The treatment is preferably performed under conditions such that the disease or condition is alleviated or improved.

Transesterification

In some embodiments, the lipid compositions are made by transesterification. In some preferred embodiments, a natural starting oil is used. Examples of suitable starting oils include Korean pine oil, Siberian pine oil, and oils from other sources identified in Table 1 above, fish oil with a high triglyceride content, a fish oil with a high phospholipid content (e.g., herring oil), a krill oil with a high phospholipid content, and marine oil concentrates comprising esters, fatty acids or triglycerides with contents of EPA and/or DHA. Transesterification is preferably used to replace fatty acids in the starting oil with a desired fatty acid. For example, a starting oil comprising a non-methylene-interrupted fatty acid moiety such as a pine oil may be transesterified with a second lipid composition comprising a desired omega-3 fatty acid moiety, a non-beta-oxidizable fatty acid moiety, or conjugated linoleic acid moiety. As another example, a starting marine oil with a high phospholipid content may be transesterified with a suitable source of non-methylene-interrupted fatty acid moieties. Methods for transesterification are provided in U.S Publ. No. 20060177486 and 20030144353, each of which is incorporated herein by reference.

In some embodiments, novel acylglycerides of the present invention are manufactured by using non-specific and position-specific lipases to insert a first fatty acyl residue at position 2 (SN2) of the acylglyceride and a second fatty acyl residue at positions 1 and 3 (SN1 and SN3) of the acylglyceride. Non-specific lipases are lipases that are able to hydrolyse or esterify (i.e., the reverse reaction) fatty acids in all positions on a glycerol. A position-specific or 1,3 specific lipase almost exclusively hydrolyses or esterifies fatty acids in position 1 and 3 on the glycerol backbone. The structured acylglycerides of the present invention are synthesized by first using a non-specific lipase to attach the desired fatty acid for position 2 to all 3 positions and then hydrolysing the acyl residues in position 1 and 3 using a 1,3 specific lipase. The hydrolysed acids are then removed by distillation before the acids desired to be attached to positions 1 are 3 are added and esterified to position 1 and 3 by the same lipase. The direction of the reaction (hydrolysis or esterification) is easily controlled by water addition or removal respectively. In the following example is a general outline of the method.

In particularly preferred embodiments, a purified aliquot of a first fatty acid (about 3 moles), glycerol (about 1 mole) and up to 10% by weight of acids are mixed with immobilized non-specific lipase (commercially available). The mixture is stirred under vacuum and slightly heated (50-60 C). The water produced during the esterification is continuously removed by the vacuum suction. After 24-48 hours, the reaction is finished and the enzymes are removed and recovered by filtration. The resulting acylglyceride has the first fatty acid attached at all three positions. The first fatty acid residue at positions 1 and 3 is then removed in by addition of 1,3 specific immobilized lipase (commercially available) and 1% water. The mixture is heated to 50-60 C. and stirred under nitrogen atmosphere for 24-48 hours. The reaction mixture now comprises free fatty acids liberated from position 1 and 3 and monoglycerides (fatty acid B attached to position 2). Next, in preferred embodiments, the fatty acids are distilled off from the mixture by molecular distillation. In further preferred embodiments, about one mole of the monoglyceride is allowed to react for 24-48 hours with 2 moles a second free fatty acid in the presence of 1,3 specific lipase. In some embodiments, this reaction takes place under stirring and vacuum at 50-60.degree. C. to remove water produced in the esterification process. The resulting acylglyceride is a structured triglyceride with the first fatty acid in position 2 and the second fatty acid in positions 1 and 3.

As described above, in some embodiments of the present invention, lipase that specifically acts on the positions 1 and 3 of triglyceride is used as catalyst. The present invention is not limited to the use of any particular 1,3 specific lipase. Examples of 1,3 specific lipases useful in the present invention include lipases produced by a microorganism belonging to the genus *Rhizopus, Rhizomucor, Mucor, Penicillium, Aspergillus, Humicola* or *Fusarium*, as well as porcine pancreatic lipase. Examples of commercially available lipases include lipase of *Rhizopus delemar* (Tanabe Pharmaceutical, Dalipase), lipase of *Rhizomucor miehei* (Novo Nordisk, Ribozyme IM), lipase of *Aspergillus niger* (Amano Pharmaceutical, Lipase A), lipase of *Humicola lanuginosa* (Novo Nordisk, Lipolase), lipase of *Mucor javanicus* (Amano Pharmaceutical, Lipase M) and lipase of *Fusarium heterosporum*. These lipases may be used in their native form, or in the form of lipase that has been immobilized on cellite, ion exchange resin or a ceramic carrier.

The amount of water added to the reaction system affects the outcome of the reaction. Transesterification does not proceed in the absolute absence of water, while if the amount of water is too much, hydrolysis occurs, the triglyceride recovery rate decreases, or spontaneous acyl group transfer occurs in a partially acylated glyceride resulting in transfer of the saturated fatty acid at the position 2 to the position 1 or 3. Thus, when using an immobilized enzyme that does not have bonded water, it is effective to first activate the enzyme using a substrate to which water has been added before carrying out the reaction, and then use a substrate to which water is not added during the reaction. In order to activate the enzyme in batch reactions, a substrate containing water at 0 to 1,000% (wt %) of the amount of added enzyme should be used to pretreat the enzyme, and in the case of activating by a column method, a water-saturated substrate should be allowed to continuously flow through the column. The amount of lipase used in a batch reaction may be determined according to the reaction conditions. Although there are no particular limitations on the amount of lipase, 1 to 30% (wt %) of the reaction mixture is suitable when using, for example, lipase of *Rhizopus delemar* or lipase of *Rhizomucor miehei* immobilized on cellite or a ceramic carrier.

In some preferred embodiments, the above-mentioned immobilized enzyme can be used repeatedly. Namely, the reaction can be continued by leaving the immobilized enzyme in a reaction vessel after reaction and replacing the reaction mixture with freshly prepared reaction mixture comprising substrate. In addition, for transesterification by a column method, a reaction mixture containing substrate be allowed to flow continuously at the rate of 0.05 to 20 ml/hr per gram of enzyme. In other preferred embodiments, the content of target triglyceride can be increased by performing transesterification repeatedly. Namely, lipase specifically acting on the positions 1 and 3 of the acylglyceride is allowed to act in the presence of the second fatty acid or an ester thereof to obtain a reaction mixture in which fatty acids at positions 1 and 3 are transesterified to the desired fatty acid.

The target acylglycerides of the present invention can easily be isolated by routine methods such as liquid chromatography, molecular distillation, downstream membrane fractionation or vacuum superfractionation or a combination thereof. Purification of the target acylglycerides of the present invention can be performed by alkaline deacidation, steam distillation, molecular distillation, downstream membrane fractionation, vacuum superfractionation, column chromatography, solvent extraction or membrane separation, or a combination thereof so as to remove the above-mentioned fatty acids released by the transesterification and unreacted unsaturated fatty acids.

In some embodiments, the present invention utilizes a phospholipid, preferably a phosphatide such as lecithin (e.g., egg lecithin, krill lecithin, herring lecithin, soybean lecithin, or egg lecithin), in an enzymatic reaction so that the fatty acid in position 1 of the phospholipid is replaced with a desired fatty acid residue. The present invention is not limited to the use of any particular phospholipid. Indeed, the use of a variety of phospholipids is contemplated. In some embodiments, the phospholipid is a phosphatidic or lysophosphatidic acid. In more preferred embodiments, the phospholipid is a mixture of phosphatides such as phosphatidylcholine, phosphatidylethanolamine, phosphatidylserine and phosphatidylinositol. The present invention is not limited to the use of any particular source of phospholipids.

In preferred embodiments, the replacement (e.g., by transesterification) of the phospholipid fatty acids with a desired fatty acid or the addition (e.g. esterification) is catalyzed by a lipase. The present invention is not limited to the use of any particular lipase. Indeed, the use of a variety of lipases is contemplated, including, but not limited to, the aforementioned *Thermomyces lanuginosus* lipase, *Rhizomucor miehei* lipase, *Candida antarctica* lipase, *Pseudomonas* fluorescence lipase, and *Mucor javanicus* lipase. It is contemplated that a variety of desired fatty acids may be substituted onto the phospholipids utilized in the process of the present invention, especially fatty acids that are not initially present in the starting phospholipid composition such as a non-methylene-interrupted fatty acid moiety and a second bioactive lipid moiety, an omega-3 fatty acid moiety, a non-beta-oxidizable fatty acid moiety, a conjugated linoleic acid moiety and combinations thereof Chemical Synthesis Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent (Hermetter; Chemistry and Physics of lipids, 1981, 28, 111). Sn-Glycero-3-phosphocholine, as cadmium (II) adduct can also be reacted with the imidazolide activated fatty acid in the presence of DBU (1,8-diazabicyclo[5.4.0]undec-7-ene] to prepare the phosphatidylcholine of the respective fatty acid (International application number PCT/GB2003/002582). Enzymatic transphosphatidylation can affect the transformation of phosphatidylcholine to phosphatidylethanolamine (Wang et al, J. Am. Chem. Soc., 1993, 115, 10487). In other embodiments, a lysophospholipid with a desired bioactive fatty acid moiety (e.g., omega-3 fatty acid moiety, conjugated linoleic acid moiety of sciadonic acid moiety) at the SN-1 or SN-2 position is acylated with a non-beta-oxidizable fatty acid analogue moiety by combining desired omega-3 fatty acid non-beta-oxidizable fatty acid analogue moiety anhydride (e.g. from TTA) and 4-pyrrolidinopyridine as a catalyst (1.2 equivalents) in alcohol-free chloroform. Polyunsaturated fatty acids containing phospholipids may be prepared by various ways, mainly by chemical synthesis of phospholipids as described, by enzymatic esterification and transesterification of phospholipids or enzymatic transphosphatidylation of phospholipids. (Hosokawa, J. Am. Oil Chem. Soc. 1995, 1287, Lilja-Hallberg, Biocatalysis, 1994, 195).

Isolation of Phospholipids from a Living Organism, Consortium, or System

In some embodiments, the technology relates to isolating phospholipids (e.g., a natural phospholipid and/or an oil) comprising a desired fatty acid moiety or combination of fatty acid moieties (e.g., non-methylene-interrupted fatty acid moiety, an omega-3 fatty acid moiety, a non-beta-oxidizable fatty acid moiety, a conjugated linoleic acid moiety and combinations thereof) from one or more living organisms such as a bacterium, alga, archaeon, yeast, etc. Phospholipids make up approximately 10% of the dry weight of a cell. Thus, cultures of cells provide a source for the production and harvesting of phospholipids. Accordingly, in some embodiments, the technology relates to feeding a living organism a desired fatty acid moiety or combination, which is then incorporated into phospholipid by the living organism, and then isolating the phospholipid, e.g., by biochemical or other isolation and/or purification techniques. In some embodiments, the phospholipid is co-isolated with other biological molecules, substances, entities, etc. that are produced by the living organism. That is, in some embodiments, the technology relates to a composition (e.g., an oil) and/or a method of producing a composition produced from a living organism, wherein the composition comprises a phospholipid (e.g., a natural phospholipid) having one or more desired fatty acid moieties (non-methylene-interrupted fatty acid moiety, an omega-3 fatty acid moiety, a non-beta-oxidizable fatty acid moiety, a conjugated linoleic acid moiety and combinations thereof) and optionally at least one other biological molecule from the living organism.

The living organism may, in some embodiments, be grown in a controlled culture, e.g., in a defined medium, a semi-defined medium, an undefined medium, a synthetic medium, or a natural medium; under controlled temperature, pressure, volume, and agitation; and in a controlled atmosphere of gases (e.g., a particular mixture of oxygen, carbon dioxide, nitrogen, and other gases, etc.). The culture may comprise a single type of organism (e.g., a single species, sub-species, clone, subtype, isolate, etc.) or the culture may comprise more than one type of organism (e.g., more than one species, sub-species, clone, subtype, isolate, etc.).

In some embodiments, the living organism is a member of the Bacteria; in some embodiments, the living organism is a member of the Eukarya; and, in some embodiments, the living organism is a member of the Archaea, as defined by, e.g., Woese C, Fox G (1977). "Phylogenetic structure of the prokaryotic domain: the primary kingdoms." *Proc Natl Acad Sci USA* 74: 5088-90; Woese C, Kandler O, Wheelis M (1990). "Towards a natural system of organisms: proposal for the domains Archaea, Bacteria, and Eucarya." *Proc Natl Acad Sci USA* 87: 4576-9. In some embodiments, one or more phospholipids according to the technology is or are isolated from a composition of more than one living organism, e.g., a co-culture and/or living system and/or consortium of living organisms that may or may not be categorized in the same phylogenetic kingdom.

It is contemplated that any organism that can be grown in the presence of the desired fatty acid moiety is encompassed by the present technology. It is contemplated that any organism that can incorporate a desired fatty acid moiety into a phospholipid is encompassed by the present technology.

Further Aspects

In some embodiments, the compositions provided herein are combined with a liposome or formulated into a micellar form to assist in administration. In some embodiments, compounds are formulated in a cochleate delivery vehicle. Cochleate delivery vehicles are a new technology platform for oral delivery of drugs. Cochleates are stable phospholipid-cation precipitates composed of simple, naturally occurring materials, for example, phosphatidylserine and calcium. Cochleates are a potential nanosized system that can encapsulate hydrophobic, amphiphilic, negatively, or positively charged moieties.

In some embodiments, the compound is an isolated form or purified form. For example, the compound may be in a form or at a purity other than that found in a biological system such as in vivo. In some embodiments, the compound is semi-isolated or semi-purified, e.g., the compound is an isolated form or purified form and is present in a composition with one or more other biological molecules that are not contaminants or impurities. In some embodiments, the compounds provided are formulated to provide a pharmaceutical composition comprising a compound according to the technology and/or a pharmaceutically acceptable carrier, diluent, excipient, or adjuvant.

An addition, embodiments provide compounds that are lipids comprising at least one non-polar moiety and a polar moiety, wherein the non-polar moiety is of the formula X—Y—Z—, wherein X is a hydrocarbyl chain; Y is S, Se, $SO_2$, SO, O, or $CH_2$; and Z is an optional hydrocarbyl group. Furthermore, when Y is $CH_2$, the chain X—Y—Z contains an even number of atoms, the polar moiety is —$[C(O)]_m$ PHG, wherein PHG is a polar head group and m is the number of non-polar moieties.

Pharmaceutical Compositions

Provided herein are pharmaceutical compositions comprising a therapeutically effective amount of a composition according to the present technology and a pharmaceutically acceptable carrier, diluent, or excipient (including combinations thereof).

A composition according to the technology comprises or consists of a therapeutically effective amount of a pharmaceutically active agent. In some embodiments, it includes a pharmaceutically acceptable carrier, diluent, or excipient (including combinations thereof). Acceptable carriers or diluents for therapeutic use are well known in the pharmaceutical art and are described, for example, in Remington's Pharmaceutical Sciences, Mack Publishing Co. (A. R. Gennaro edit. 1985). The choice of pharmaceutical carrier, excipient, or diluent is selected with regard to the intended route of administration and standard pharmaceutical practice. The pharmaceutical comprise as, or in addition to, the carrier, excipient, or diluent any suitable binder(s), lubricant(s), suspending agent(s), coating agent(s), and/or solubilizing agent(s).

This pharmaceutical composition will desirably be provided in a sterile form. It may be provided in unit dosage form and will generally be provided in a sealed container. A plurality of unit dosage forms may be provided.

Pharmaceutical compositions within the scope of the present technology may include one or more of the following: preserving agents, solubilizing agents, stabilizing agents, wetting agents, emulsifiers, sweeteners, colorants, flavoring agents, odorants, and/or salts. Compounds of the present technology may themselves be provided in the form of a pharmaceutically acceptable salt. In addition, embodiments may comprise buffers, coating agents, antioxidants, suspending agents, adjuvants, excipients, and/or diluents. Examples of preservatives include sodium benzoate, sorbic acid, and esters of p-hydroxybenzoic acid.

They may also contain other therapeutically active agents in addition to compounds of the present technology. Where two or more therapeutic agents are used they may be administered separately (e.g., at different times and/or via different routes) and therefore do not always need to be present in a single composition. Thus, combination therapy is within the scope of the present technology.

Route of Administration

A pharmaceutical composition within the scope of the present technology may be adapted for administration by any appropriate route. For example, it may be administered by the oral (including buccal or sublingual), rectal, nasal, topical (including buccal, sublingual, or transdermal), vaginal, or parenteral (including subcutaneous, intramuscular, intravenous, or intradermal) routes. Such a composition may be prepared by any method known in the art of pharmacy, for example, by admixing one or more active ingredients with a suitable carrier.

In various embodiments, different drug delivery systems are used to administer pharmaceutical compositions of the present technology, depending upon the desired route of administration. Drug delivery systems are described, for example, by Langer (*Science* 249:1527-1533 (1991)) and by Illum and Davis (*Current Opinions in Biotechnology* 2: 254-259 (1991)).

The agents of the present technology may be administered alone but will generally be administered as a pharmaceutical composition—e.g., the agent is in admixture with a suitable pharmaceutical excipient, diluent, or carrier selected with regard to the intended route of administration and standard pharmaceutical practice. For example, in some embodiments the agent is administered (e.g., orally or topically) in the form of tablets, capsules, ovules, elixirs, solutions, or suspensions, which may contain flavoring or coloring agents, for immediate, delayed, modified, sustained, pulsed, and/or controlled-release applications.

In some embodiments, tablets contain excipients such as microcrystalline cellulose, lactose, sodium citrate, calcium carbonate, dibasic calcium phosphate and/or glycine; disintegrants such as starch (preferably corn, potato, or tapioca starch), sodium starch glycollate, croscarmellose sodium, and/or certain complex silicates; and/or granulation binders such as polyvinylpyrrolidone, hydroxypropylmethylcellulose (HPMC), hydroxypropylcellulose (HPC), sucrose, gelatin, and/or acacia. Additionally, lubricating agents such as magnesium stearate, stearic acid, glyceryl behenate, and talc may be included.

In some embodiments, solid compositions of a similar type are also employed as fillers in gelatin capsules. Examples of excipients in this regard include lactose, starch, a cellulose, milk sugar, or high molecular weight polyethylene glycols. For some embodiments of aqueous suspensions and/or elixirs, the agent is combined with various sweetening or flavoring agents, coloring matter or dyes, with emulsifying and/or suspending agents and with diluents such as water, ethanol, propylene glycol, and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual.

It is to be understood that not all of the agent need be administered by the same route. Likewise, if the composition comprises more than one active component, then those components may be administered by different routes.

If the agent of the present technology is administered parenterally, then examples of such administration include one or more of: intravenously, intra-arterially, intraperitoneally, intrathecally, intraventricularly, intraurethrally, intrasternally, intracranially, intramuscularly, or subcutaneously administering the agent; and/or by using infusion techniques.

Oral Administration

In some embodiments, pharmaceutical compositions adapted for oral administration are provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g., vegetable oils) may be used to provide oil-in-water or water-in-oil suspensions. An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis, e.g., as described in *Pharmaceutical Research,* 3: 318 (1986)).

Topical Administration

Alternatively, the agent of the present technology can be administered in the form of a suppository or pessary, or it may be applied topically in the form of a gel, hydrogel, lotion, solution, cream, ointment or dusting powder. The agent of the present technology may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present technology can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Rectal Administration

Pharmaceutical compositions adapted for rectal administration may be provided as suppositories or enemas.

Nasal Administration

Pharmaceutical compositions adapted for nasal administration may use solid carriers, e.g., powders (e.g., having a particle size in the range of 20 to 500 microns). Powders can be administered in the manner in which snuff is taken, e.g., by rapid inhalation through the nose from a container of powder held close to the nose. Compositions adopted for nasal administration may alternatively use liquid carriers, e.g., nasal sprays or nasal drops. These may comprise aqueous or oil solutions of the active ingredient. Compositions for administration by inhalation may be supplied in specially adapted devices, e.g., in pressurized aerosols, nebulizers, or insufflators. These devices can be constructed so as to provide predetermined dosages of the active ingredient Vaginal Administration Pharmaceutical compositions adapted for vaginal administration may be provided as pessaries, tampons, creams, gels, pastes, foams or spray formulations.

Parenteral Administration

If the agent of the present technology is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Transdermal; Transmucosal; Transurethral or Intraurethral

"Transdermal" refers to the delivery of a compound by passage through the skin and into the blood stream. "Transmucosal" refers to delivery of a compound by passage of the compound through the mucosal tissue and into the blood stream. "Transurethral" or "intraurethral" refers to delivery of a drug into the urethra, such that the drug contacts and passes through the wall of the urethra and enters into the blood stream.

Penetration Enhancement or Permeation Enhancement

"Penetration enhancement" or "permeation enhancement" refers to an increase in the permeability of the skin or mucosal tissue to a selected pharmacologically active compound such that the rate at which the compound permeates through the skin or mucosal tissue is increased.

Penetration enhancers may include, for example, dimethylsulfoxide (DMSO); dimethyl formamide (DMF); N,N-dimethylacetamide (DMA); decylmethylsulfoxide (CI-OMSO); polyethyleneglycol monolaurate (PEGML); glyceral monolaurate; lecithin; 1-substituted azacycloheptanones, particularly 1-N-dodecylcyclaza-cycloheptanones (e.g., as available under the trademark Azone™ from Nelson Research & Development Co., Irvine, Calif.), alcohols, and the like.

Carriers or Vehicles

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

Examples of pharmaceutically acceptable carriers include, for example, water, salt solutions, alcohol, silicone, waxes, petroleum jelly, vegetable oils, polyethylene glycols, propylene glycol, sugars, gelatin, lactose, amylose, magnesium stearate, talc, surfactants, silicic acid, viscous paraffin, perfume oil, fatty acid monoglycerides and diglycerides, petroethral fatty add esters, hydroxymethyl-cellulose, polyvinylpyrrolidone, and the like.

Epidermal Drug Delivery (Transfersomes)

Transfersomes ("carrying bodies") are complex, most often vesicular, bi- or multi-component aggregates capable of crossing barriers and of transferring material between the application and the destination sites. Transfersomes are sold by IDEA Corporation, Munich, Germany, and TRANSFERSOME is a trade mark of that company. Transfersome transdermal drug delivery technology may be used for controllable and non-invasive delivery of a wide variety of large molecules as well as for the improved delivery of small molecules, including the metabolic enzyme antagonists and/or drugs of the present technology.

Transfersomes may be optimized to attain extremely flexible and self-regulating membranes. They are therefore deformable and consequently can cross microporous barriers efficiently, even when the available passages are much smaller than the average aggregate size. Transfersome formulations are typically composed of natural amphipatic compounds suspended in a water-based solution, optionally containing biocompatible surfactants. Vesicular Transfersomes consist of a lipid bilayer surrounding an aqueous core and further contain at least one component, capable of softening the membrane. The bilayer of a Transferosome is therefore more flexible than a liposome membrane, even metastable. Transfersome vesicles consequently change their shape easily by adjusting locally to ambient stress.

Skin is one of the best biological barriers. Its outermost part reaches less than 10% into the depth of the skin but contributes over 80% to the skin permeability barrier. This body protecting layer consists of overlapping, flaccid corneocytes, organized in columnar clusters, sealed with multilamellar lipid sheets that are covalently attached to the cell membranes and very tightly packed. Generally, the average number of, and the degree of order in, the intercellular lipid lamellae increases toward the skin surface. This is accompanied by a continuous, but nonlinear, decrease in local water content near the surface. Notwithstanding this, the peak skin barrier is located in the inner half of the outermost layer, where the intercellular lipid seals are already formed, but not yet compromised by the skin cells detachment.

Passage of transfersome aggregates across the skin is a function of vesicle membrane flexibility, hydrophilicity, and the ability to retain vesicle integrity, while the aggregate undergoes a significant change in shape. When a suspension of Transfersome vesicles is placed on the surface of the skin, water evaporates from the relatively arid skin surface and the vesicles start to dry out. Due to the strong polarity of major Transfersome ingredients, the large number of hydrophilic groups on the membrane, assisted by the softness of the membrane, the vesicles are attracted to the areas of higher water content in the narrow gaps between adjoining cells in the skin barrier, enabling skin penetration of the vehicle. This, together with the vesicle's extreme ability to deform, enables Transfersome aggregates to open, temporarily, the tiny "cracks" through which water normally evaporates out of the skin Channels between the skin cells, two orders of magnitude wider than the original micropores, are thus created. Such newly activated passages can accommodate sufficiently deformable vesicles, which maintain their integrity but change their shape to fit the channel Along the resulting "virtual pathways", or "virtual channels" in the outermost layer, Transfersomes reach regions of high water content in the deeper skin layers. There, the vesicles (re) distribute. Since Transfersomes are too large to enter the blood vessels locally, they bypass the capillary bed and get to subcutaneous tissue, where they accumulate.

Although small molecules that have crossed the outermost layer of the skin (stratum corneum) are normally cleared from the skin through the blood circulation, delivery of drugs by means of Transfersome vesicles allows accumulation of drug deep under the skin. Due to their large size, the vesicles are cleared slowly from the skin and associated drugs can accumulate at the site. Transfersome mediated administration of weight drugs, consequently, tends to shift the drug distribution towards the deep tissue under the application site.

Blood Brain Barrier (BBB)

Pharmaceutical compositions may be designed to pass across the blood brain barrier (BBB). For example, a carrier such as a fatty acid, inositol or cholesterol may be selected that is able to penetrate the BBB. The carrier may be a substance that enters the brain through a specific transport system in brain endothelial cells, such as insulin-like growth factor I or II. The carrier may be coupled to the active agent or may contain and/or be in admixture with the active agent. Liposomes can be used to cross the BBB. WO91/04014 describes a liposome delivery system in which an active agent can be encapsulated/embedded and in which molecules that are normally transported across the BBB (e.g., insulin or insulin-like growth factor I or II) are present on the liposome outer surface. Liposome delivery systems are also discussed in U.S. Pat. No. 4,704,355.

Polymer Delivery/Therapeutics

The agents may further be delivered attached to polymers. Polymer based therapeutics have been proposed to be effective delivery systems, and generally comprise one or more agents to be delivered attached to a polymeric molecule, which acts as a carrier. The agents are thus disposed on the polymer backbone, and are carried into the target cell together with the polymer.

The agents may be coupled, fused, mixed, combined, or otherwise joined to a polymer. The coupling, etc. between the agent and the polymer may be permanent or transient, and may involve covalent or non-covalent interactions (including ionic interactions, hydrophobic forces, Van der Waals interactions, etc.). The exact mode of coupling is not important as long as the agent is taken into a target cell substantially together with the polymer. For simplicity, the entity comprising the agent attached to the polymer carrier is referred to here as a "polymer-agent conjugate".

Any suitable polymer, for example, a natural or synthetic polymer, may be used, e.g., the carrier polymer is a synthetic polymer such as PEG. In some embodiments, the carrier polymer is a biologically inert molecule. Particular examples of polymers include polyethylene glycol (PEG), N-(2-hydroxypropyl) methacrylamide (HPMA) copolymers, polyamidoamine (PAMAM) dendrimers, HEMA, linear polyamidoamine polymers, etc. Any suitable linker for attaching the agent to the polymer may be used. In some embodiments, the linker is a biodegradable linker. Use of biodegradable linkers enables controlled release of the agent on exposure to the extracellular or intracellular environment. High molecular weight macromolecules are unable to diffuse passively into cells and are instead engulfed as membrane-encircled vesicles. Once inside the vesicle, intracellular enzymes may act on the polymer-agent conjugate to effect release of the agent. Controlled intracellular release circumvents the toxic side effects associated with many drugs.

Furthermore, agents may be conjugated, attached, etc. by methods known in the art to any suitable polymer and delivered. The agents may in particular comprise any of the molecules referred to as "second agents", such as polypeptides, nucleic acids, macromolecules, etc., as described in the section below. In particular, the agent may comprise a pro-drug as described elsewhere.

The ability to choose the starting polymer enables the engineering of polymer-agent conjugates for desirable properties. The molecular weight of the polymer (and thus the polymer-agent conjugate), as well as its charge and hydrophobicity properties, may be precisely tailored. Advantages of using polymer-agent conjugates include economy of manufacture, stability (longer shelf life), and reduction of immunogenicity and side effects. Furthermore, polymer-agent conjugates are especially useful for the targeting of tumor cells because of the enhanced permeability and retention (EPR) effect, in which growing tumors are more "leaky" to circulating macromolecules and large particles, allowing them easy access to the interior of the tumor. Increased accumulation and low toxicity (typically 10-20% of the toxicity of the free agent) are also observed. Use of hyperbranched dendrimers, for example, PAMAM dendrimers, is particularly advantageous in that they enable monodisperse compositions to be made and also flexibility of attachment sites (within the interior or the exterior of the dendrimer). The pH responsiveness of polymer-agent conjugates, for example, those conjugated to polyamindoamine polymers, may be tailored for particular intracellular environments. This enables the drug to be released only when the polymer therapeutic encounters a particular pH or range of pH, e.g., within a particular intracellular compartment. The polymer agent conjugates may further comprise a targeting means, such as an immunoglobulin or antibody, which directs the polymer-agent conjugate to certain tissues, organs or cells comprising a target, for example, a particular antigen. Other targeting means are described elsewhere in this document, and are also known in the art.

Particular examples of polymer-agent conjugates include "Smancs", comprising a conjugate of styrene-co-maleic anhydride and the antitumour protein neocarzinostatin, and a conjugate of PEG (polyethylene glycol) with L-asparaginase for treatment of leukaemia; PK1 (a conjugate of a HPMA copolymer with the anticancer drug doxorubicin); PK2 (similar to PK1, but furthermore including a galactose group for targeting primary and secondary liver cancer); a conjugate of HPMA copolymer with the anticancer agent captothecin; a conjugate of HPMA copolymer with the anticancer agent paclitaxel; HPMA copolymer-platinate, etc. Any of these polymer-agent conjugates are suitable for co-loading into the transgenic cells of the present technology.

Dose Levels

Typically, a physician will determine the actual dosage which will be most suitable for an individual subject. The specific dose level and frequency of dosage for any particular patient may be varied and will depend upon a variety of factors including the activity of the specific compound employed; the metabolic stability and length of action of that compound; the age, body weight, general health, sex, diet, mode and time of administration; rate of excretion; drug combination; the severity of the particular condition; and the individual undergoing therapy. The agent and/or the pharmaceutical composition of the present technology may be administered in accordance with a regimen of from 1 to 10 times per day, such as once or twice per day. For oral and parenteral administration to human patients, the daily dosage level of the agent may be in single or divided doses.

Depending upon the need, the agent may be administered at a dose of from 0.01 to 30 mg/kg body weight, such as from 0.1 to 10 mg/kg or from 0.1 to 1 mg/kg body weight. Naturally, the dosages mentioned herein are exemplary of the average case. There can, of course, be individual instances where higher or lower dosage ranges are merited.

Therapeutically Effective Amount

"Therapeutically effective amount" refers to the amount of the therapeutic agent that is effective to achieve its intended purpose. While individual patient needs may vary, determination of optimal ranges for effective amounts of the compounds related to the technology is within the skill of the art. Generally, the dosage regimen for treating a condition with the compounds and/or compositions of this technology is selected in accordance with a variety of factors, including the type, age, weight, sex, diet and medical condition of the patient; the severity of the dysfunction; the route of administration; pharmacological considerations such as the activity, efficacy, pharmacokinetic and toxicology profiles of the particular compound used; whether a drug delivery system is used; and whether the compound is administered as part of a drug combination and can be adjusted by one skilled in the art. Thus, the dosage regimen actually employed may vary widely and therefore may deviate from the exemplary dosage regimens set forth herein.

Pharmaceutical Combinations

In general, the agent may be used in combination with one or more other pharmaceutically active agents. Other agents are sometimes referred to auxiliary agents.

Pharmaceutically Acceptable Salt

The agent may be in the form of, and/or may be administered as, a pharmaceutically acceptable salt, e.g., an acid addition salt or a base salt, or a solvate thereof, including a hydrate thereof. For a review on suitable salts see Berge et al, *J.* (1977) *Pharm. Sci.* 66: 1-19.

Typically, a pharmaceutically acceptable salt may be readily prepared by using a desired acid or base, as appropriate. The salt may precipitate from solution and be collected by filtration or may be recovered by evaporation of the solvent.

Suitable acid addition salts are formed from acids that form non-toxic salts such as hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate, and pamoate salts.

Suitable base salts are formed from bases that form non-toxic salts and examples are sodium, potassium, aluminum, calcium, magnesium, zinc, and diethanolamine salts.

Disease States

The present technology relates to the use of a composition according to embodiments of the technology for the manufacture of a medicament for the treatment and/or prevention of a condition selected from diabetes, inflammatory disorders, metabolic syndrome, obesity, hypertension, fatty liver, diabetes, hyperglycaemia, hyperinsulinemia, and stenosis.

In some embodiments, the present technology provides use of a compound according to the technology for the manufacture of a medicament for lowering concentration of cholesterol and triglycerides in the blood of mammals and/or inhibiting the oxidative modification of low density lipoprotein.

In some embodiments, the present technology provides a method for producing weigh loss or a reduction of the fat mass in a human or non-human animal in need thereof, comprising administering thereto an effective amount of a compound of the technology or a pharmaceutically acceptable salt thereof.

In some embodiments, the present technology provides a method for the modification of the fat distribution and content of animals in order to improve the quality of the meat, or product such as milk and eggs, comprising administering thereto an effective amount of a compound of the technology or a pharmaceutically acceptable salt thereof. Preferably said animal is an agricultural animal, such as gallinaceous birds, bovine, ovine, caprine or porcine mammals. The animal may be a fish or shellfish, such as salmon, cod, Tilapia, clams, oysters, lobster or crabs.

In some embodiments, the present technology provides use of a compound according to the technology or a pharmaceutically acceptable salt thereof in the manufacture of a medicament for the inhibition and/or prevention of the growth of tumors.

In some embodiments, the present technology provides use of a compound according to the technology in the manufacture of a medicament for the inhibition and/or prevention of the invasion of a primary tumor into the connective tissue.

In some embodiments, the present technology provides use of a compound according to the technology for the manufacture of a medicament for the inhibition and/or prevention of the metastatic properties of a tumor, e.g., to inhibit the formation of secondary tumors. For example, the use of the present compounds may increase the overall survival of mammals with tumors.

In some embodiments, the present technology provides a method for the treatment and/or inhibition of primary and secondary metastatic neoplasms, comprising administering a compound of the technology or a pharmaceutically acceptable salt thereof.

In some embodiments, the present technology provides use of a compound of the technology or a pharmaceutically acceptable salt thereof in the manufacture of a medicament for the prevention and/or treatment of proliferative skin disorders such as psoriasis, atopic dermatitis, non-specific dermatitis, primary irritant contact dermatitis, allergic contact dermatitis, lamellar ichthyosis, epidermolytic hyperkeratosis, pre malignant sun induced keratosis, and seborrhea.

In some embodiments, the present technology provides use of a compound of the technology or a pharmaceutically acceptable salt thereof in the manufacture of a medicament for the inhibition of proliferation and/or induction of differentiation of keratinocytes.

In some embodiments, the present technology provides use of a compound of the technology or a pharmaceutically acceptable salt thereof in the manufacture of a medicament for the prevention and/or treatment of inflammatory disorders. For example, in some embodiments, the present technology provides use of a compound of the technology or a pharmaceutically acceptable salt thereof in the manufacture of a medicament for the prevention and/or treatment of inflammatory disorders, wherein the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myasthenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation.

In some embodiments, the present technology provides a method for enhancing the endogenous production of interleukin-10 (IL-10) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides a method for suppression of the endogenous production of interleukin-2 (IL-2) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides use of a compound of the technology or a pharmaceutically acceptable salt thereof in the manufacture of a medicament for the inhibition of proliferation of stimulated peripheral mononuclear cells (PBMC).

Further description of these and other diseases is provided below.

Obesity and Related Diseases

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, *Acanthosis nigricans*, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

In some embodiments, the present technology provides a treatment regimen that is useful in returning the body weight of obese subjects toward a normal body weight. In some embodiments, the technology provides a therapy for obesity that results in maintenance of the lowered body weight for an extended period of time. Further, in some embodiments the present technology reduces or inhibits the weight gain normally induced by fat rich diets.

In some embodiments, the present technology prevents obesity and, once treatment has begun, to arrests progression or prevents the onset of diseases that are the consequence of, or secondary to, the obesity, such as hypertension and fatty liver.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficiency, normal variant short stature, Turner's syndrome, and other pathological conditions showing reduced metabolic activity.

In some embodiments, the present technology provides a treatment regimen that is useful in lowering the blood pressure. Further, in some embodiments the present technology provides a treatment regimen that is useful in lowering the concentration of triacylglycerols in the liver. It is anticipated that such a regimen provides an inhibiting effect on the development of a fatty liver condition and is suited as a method for the treatment of the manifested disease.

In some embodiments, the compounds of the present technology activate the oxidation, and also reduce the concentration, of triglycerides in the liver.

The term "metabolic syndrome" is used to describe a multimetabolic syndrome that is inter alia characterized by hyperinsulinemia, insulin resistance, obesity, glucose intolerance, Type 2 diabetes mellitus, dyslipidemia, or hypertension.

As indicated above it is anticipated that the compounds of the present technology provide a positive effect on all the conditions mentioned above, e.g., by regulating both glucose and lipid homeostasis, and thus it is anticipated that the compounds of the present technology are suitable agents for the regulation of the above defined metabolic disease (sometimes called syndrome X).

Diabetes

There are two major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture; the nearly total disappearance of insulin-producing pancreatic beta cells which results in hyperglycemia.

Considerable evidence has been accumulated showing that most IDDM is the consequence of progressive beta-cell destruction during an asymptomatic period often extending over many years. The prediabetic period is recognized usually by the detection of circulating islet-cell autoantibodies and insulin autoantibodies.

As such, there is a need for a compound that is nontoxic and has no or minimal side effects but that would prevent clinical IDDM and NIDDM.

Type I diabetes: severe diabetes mellitus, usually of abrupt onset prior to maturity, characterized by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterized by normal to high absolute plasma insulin levels which are relatively low in relation to plasma glucose levels; also referred to as NIDDM.

Type I and II diabetes are in accordance with an etiologic classification considered as primary diabetes respectively.

Secondary diabetes comprises pancreatic, extrapancreatic and/or endocrine or drug-induced diabetes. Further, some types of diabetes are classified as exceptional forms. These include lipoatrophic, myatonic diabetes, and a type of diabetes caused by disturbance of insulin receptors.

Considering the high prevalence of diabetes in our society and the serious consequences associated therewith as discussed above, any therapeutic drug potentially useful for the treatment and prevention of this disease would have a profound beneficial effect on their health. There is a need in the art for a drug that reduces the concentration of glucose in the blood of diabetic subjects without significant adverse side effects.

Accordingly, in some embodiments, the present technology provides a treatment regimen that is useful in lowering the blood glucose and to treat a diabetic condition. Moreover, in some embodiments, the present technology provides a treatment regimen that is useful in lowering the concentration of insulin in the blood, and to increase the effect of the remaining insulin. In some preferred embodiments, the compositions of the present invention are useful for ameliorating the symptoms of diabetes, providing nutritional support to a subject with diabetes, promoting healthy blood sugar levels, supporting efficient insulin production and secretion, and/or supporting healthy glucose metabolism.

Stenosis

Many pathological conditions have been found to be associated with smooth muscle cell proliferation. Such conditions include restenosis, arteriosclerosis, coronary heart disease, thrombosis, myocardial infarction, stroke, smooth muscle neoplasms such as leiomyoma, and leiomyosarcoma of the bowel and uterus and uterine fibroid or fibroma.

Over half a million interventional intravascular procedures are performed each year. While such invasive procedures continue to improve over time, as many as 30% to 50% of the procedures performed each year fail as a result of restenosis, e.g., the formation of secondary stenosis. The reduction of restenosis is, therefore, often cited as the most critical factor in increasing the success realized in the treatment of cardiovascular disease through the use of interventional intravascular procedures, such as angioplasty, atherectomy, and procedures utilizing stents, and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using X-ray visualization. The deflated balloon is advanced until it reaches the site of the luminal narrowing, at which point the physician inflates the balloon one or more times to a pressure of about 4-6 atm for about 60 seconds. When inflated, the balloon cracks and fractures the plaque and stretches the muscle fiber in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterized by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2-3 days of these procedures and to proliferate for several days thereafter (intimal hyperplasia).

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilization and proliferation. It would be highly advantageous to develop new compositions or methods for inhibiting stenosis, restenosis or related disorders due to proliferation and mobilization of vascular smooth muscle cells following, for example, traumatic injury to vessels rendered during vascular surgery.

Accordingly, it is anticipated that embodiments of compounds in accordance with the present technology are effective in the treatment of these diseases.

Tumors

The development of new and more effective chemotherapeutic agents for cancer treatment requires considering a variety of factors including cytotoxicity, tumor cell proliferation, invasion, and metastasis. Conventional anticancer agents have typically been identified on the basis of their cytotoxicity alone.

Tumor progression is thought to occur when variant cells having selective growth properties arise within a tumor cell population, and one of the final stages of tumor progression is the appearance of the metastatic phenotype.

During metastasis, the tumor cells invade the blood vessels, survive against circulating host immune defenses, and then extravasate, implant, and grow at sites distant from the primary tumor. This ability of tumor cells to invade neighboring tissues and to colonize other organs is among the leading causes of cancer related deaths.

The term metastasis encompasses a number of phenotypic traits that together result in the clinical problem that most often leads to death from cancer. The cells lose their adherence and restrained position within an organized tissue, move into adjacent sites, develop the capacity both to invade and to egress from blood vessels, and become capable of proliferating in unnatural locations or environments. These changes in growth patterns are accompanied by an accumulation of biochemical alterations that have the capacity to promote the metastatic process.

So far, little is known about the intrinsic mechanism involved in the metastatic cascade. It is likely that in some cases the augmented metastatic potential of certain tumor cells may be due to an increased expression of oncogenes, which normally are responsible for control of various cellular functions, including differentiation, proliferation, cell motility, and communication. Further, it has been shown that substances that modulate signal transduction pathways can inhibit the metastatic behavior of a tumor, and it is also speculated that compounds with surface related effects, e.g., compounds that modulates the cell membranes, might be involved in the process leading to metastasis.

Cancer is a disease of inappropriate tissue accumulation. This derangement is most evident clinically when tumor tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumor tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity. Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumors are composed mostly of non-cycling cells, it is not surprising that chemotherapy is not always effective in eradicating cancer.

The strategy of cancer treatment is to shift tumor cells from a non-cycling compartment to a cycling compartment. Several methods that promote this shift form the basis for combined-modality treatment. Surgery is most commonly used to reduce tumor size and thus facilitate re-entry of cancer cells into the cell cycle. After the primary tumor is completely removed, microscopic metastases may remain at distant sites. Because of their small size, the micrometastases are composed principally of cycling cells Small numbers of cells that remain at primary tumor site are also likely to re-enter the cell cycle. Thus, the remaining cancer cells are often susceptible to chemotherapy. Radiation therapy or chemotherapy alone can also be used to reduce tumor bulk and thus recruit cells into the cycling cell compartment.

Combination drug therapy is, therefore, the basis for most chemotherapy employed at present. Combination chemotherapy uses the different mechanisms of action and cytotoxic potentials of multiple drugs. However, even though the chemotherapeutic agents are more effective in killing or damaging malignant cells than normal cells, the fact that they do harm normal cells indicates their great potential for toxicity. For chemotherapy to be effective, the patient must be in good physiologic condition.

Cancer treatment requires inhibition of a variety of factors including tumor cell proliferation, metastatic dissemination of cancer cells to other parts of the body, invasion, tumor-induced neovascularization, and enhancement of host immunological responses and cytotoxicity.

Conventional cancer chemotherapeutic agents have often been selected on the basis of their cytotoxicity to tumor cells. However, some anticancer agents have adverse effects on the patient's immunological system. Unfortunately, for the vast majority of conventional antineoplastic agents the margin between an effective dose and a toxic dose, e.g., the therapeutic index, is extremely low. Thus, it would be greatly advantageous if a cancer therapy or treatment could be developed that would afford noncytotoxic protection against factors that might lead to growth, progression and metastasis of invasive cancers.

Accordingly, in some embodiments, the present technology provides a method for the prevention and/or treatment of primary and metastatic neoplasms that involves using a fatty acid analogue, or a lipid comprising a fatty acid analogue, of the present technology to treat a patient suffering from a cancer.

The two essential features of cancer are invasion and metastasis. At one extreme, microinvasion of the basement membrane characterizes the transition from neoplasia to cancer, and at the other extreme, metastases generally lead to death. Invasion into the underlying connective tissue by primary tumor proceeds in stages and is facilitated by various mediators produced by the tumor cells. Tumor cells that have not invaded the basement membrane and remain confined within the epithelium are termed carcinoma in situ. Metastases, on the other hand, may form when circulating tumor cells with adherent lymphocytes and platelets are trapped in capillaries and the tumor cell membrane interacts with the capillary endothelium. The capillary endothelial junctions retract, and tumor cell ligands bind to receptors on the endothelial and basement membranes.

Tumor cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumor cells then may proliferate and synthesise platelet aggregatory factors such as thromboxanes and procoagulants, thereby leading to the deposition of a fibrin cocoon around the cells. Such a cocoon may protect the micrometastasis from attack by the host's immune system.

Cancers that can be prevented and/or treated by the compositions and methods of the present technology include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

Skin Disorders

Proliferative skin diseases are widespread throughout the world and afflict millions of humans and their domesticated animals. Proliferative skin diseases are characterized by keratinocyte cell proliferation, or division, and may also be associated with incomplete epidermal differentiation. Psoriasis is the most serious of the proliferative skin diseases with which this technology is concerned.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface.

Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma. Lesions are often localized to the extensor surfaces of the extremities, and the nails and scalp are also commonly involved.

Therapeutic efforts in psoriasis are aimed at decreasing the proliferative rate of the epidermis, either by direct action on cell division or indirectly by reducing the immunological response. For patients with localized, limited psoriasis, administration of topical corticosteroids is the most convenient outpatient therapy.

Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception.

Etretinate, like other retinoids, can produce elevations in cholesterol and triglyceride levels; therefore dietary regulation may be necessary. In addition, because etretinate can induce hepatotoxicity, liver function tests should be performed before and at regular intervals during use of the drug.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases.

Inflammatory and Auto-Immune Disorders

Interleukins, interferons, colony stimulating factors and TNF-alpha are examples of a group of diverse multi-functional proteins called cytokines. Cytokines are a class of secreted soluble proteins normally present in very low concentration in a variety of cells. Lymphoid, inflammatory hemopoietic, and other cells such as connective tissue cells (e.g. fibroblasts, osteoblasts) secrete a variety of cytokines which regulate the immune, inflammatory, repair, and acute phase responses by controlling cell proliferation, differentiation, and effector functions. The effects of cytokines are mediated through binding to high affinity receptors on specific cell types.

An important cytokine is IL-10, a 35-40 kDa peptide produced by helper T-cells, B-cells, monocytes, macrophages, and other cell types. In vitro, IL-10 has demonstrated immunosuppressive properties as evidenced by its ability to suppress cytokine production including IL-1 and TNFa. IL-10 also inhibits activation of other inflammatory cytokines, and therefore has potent anti-inflammatory activity.

It has been of recent interest to administer-IL-10 in the treatment of certain conditions characterized by excessive IL-1 and TNF-alpha production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells. Similarly, IL-10 was shown to inhibit bone marrow metastasis in severe combined immunodeficient mice.

The above conventional approaches to treating conditions characterized by excessive IL-1 and TNF-alpha production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract. None of the above approaches suggests enhancing endogenous IL-10 production in mammals for prophylaxis and treatment of diseases or conditions.

Further, it is known that IL-10 is a powerful deactivator of macrophages and T cells, and inadequate production has been implicated in various autoimmune and inflammatory disorders.

In addition, or in the alternative, embodiments of the compound or composition of the present technology are useful in the treatment of the following disorders: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumor growth, invasion and spread, angiogenesis, metastases, malignant, ascites and malignant pleural effusion; cerebral ischemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, embodiments of the compound or composition of the present technology are useful in the treatment of the following disorders: cytokine and cell proliferation/differentiation activity; immunosuppressant or immunostimulant activity (e.g., for treating immune deficiency, including infection with human immune deficiency virus; regulation of lymphocyte growth; treating cancer and many autoimmune diseases, and to prevent transplant rejection or induce tumor immunity); regulation of hematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilizing specific cell types to sites of injury or infection); hemostatic and thrombolytic activity (e.g. for treating hemophilia and stroke); anti-inflammatory activity (for treating e.g. septic shock or Crohn's disease); as antimicrobials; modulators of e.g. metabolism or behavior; as analgesics; treating specific deficiency disorders; in treatment of e.g. psoriasis, in human or veterinary medicine.

In addition, or in the alternative, embodiments of the composition of the present technology are useful in the treatment of the following disorders: macrophage inhibitory and/or T cell inhibitory activity and thus, anti-inflammatory activity; anti-immune activity, e.g., inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g., retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chorea, myasthenia gravis, pseudo-tumor cerebri, Down's Syndrome, Hunting-ton's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Treatment

Embodiments of the technology include any therapeutic application that can benefit a human or non-human animal, for example a mammal. As such, both human and veterinary treatments are within the scope of the present technology.

Treatment may be in respect of an existing condition or it may be prophylactic. It may be of an adult, a juvenile, an infant, a fetus, or a part of any of the aforesaid (e.g., an organ, tissue, cell, or nucleic acid molecule).

In some embodiments, an active agent for use in treatment is administered via any appropriate route and at any appropriate dosage. Dosages can vary between wide limits, depending upon the nature of the treatment, the age and condition of the individual to be treated, etc., and a physician will ultimately determine appropriate dosages to be used. However, without being bound by any particular dosages, a daily dosage of a compound of the present technology of from 1 µg to 1 mg/kg body weight may be suitable. The dosage may be repeated as often as appropriate. If side effects develop, the amount and/or frequency of the dosage can be reduced, in accordance with good clinical practice.

Polymorphic Form(s) and/or Asymmetric Carbon(s)

Embodiments of compounds according to the present technology may exist in a polymorphic form. In addition, embodiments of compounds according to the present technology may contain one or more asymmetric carbon atoms and therefore exist in two or more stereoisomeric forms. Where an agent contains an alkenyl or alkenylene group, cis (E) and trans (Z) isomerism may also occur. The present technology includes the individual stereoisomers of the agent and, where appropriate, the individual tautomeric forms thereof, together with mixtures thereof.

Separation of diastereoisomers and/or cis and trans isomers may be achieved by conventional techniques, e.g., by fractional crystallisation, chromatography, or H.P.L.C. of a stereoisomeric mixture of the agent or a suitable salt or derivative thereof. An individual enantiomer of a compound of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Isotopic Variations

The present technology also includes all suitable isotopic variations of the agent or a pharmaceutically acceptable salt thereof. An isotopic variation of an agent of the present technology or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2$H, $^3$H, $^{13}$C, $^{15}$N, $^{17}$O, $^{18}$O, $^{31}$P, $^{32}$P, $^{35}$S, $^{18}$F, and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, e.g., $^3$H, and carbon-14, e.g., $^{14}$C, isotopes are particularly useful for their ease of preparation and detectability. Further, substitution with isotopes such as deuterium, e.g., $^2$H, may afford certain therapeutic advantages resulting from greater metabolic stability, for example, increased in vivo half-life or reduced dosage requirements and hence may be preferred in some circumstances. Isotopic variations of the agent of the present technology and pharmaceutically acceptable salts thereof of this technology can generally be prepared by conventional procedures using appropriate isotopic variations of suitable reagents.

Pro-Drug

In some embodiments, compounds according to the technology are derived from a prodrug. Prodrugs are entities that may or may not possess pharmacological activity as such, but may be administered (such as orally or parenterally) and thereafter subject to bioactivation (for example metabolized) in the body to form the agent of the present technology which is pharmacologically active. Examples of prodrugs include entities that have certain protected group(s) and that may not possess pharmacological activity as such, but may, in certain instances, be administered (such as orally or parenterally) and thereafter metabolized in the body to form the agent of the present technology that are pharmacologically active.

Pro-Moiety

In some embodiments, the technology encompasses certain moieties known as "pro-moieties", for example as described in "Design of Prodrugs" by H. Bundgaard, Elsevier, 1985 (the disclosure of which is hereby incorporated by reference). In some embodiments, a pro-moiety may be placed on appropriate functionalities of the agents. Such prodrugs are also included within the scope of the technology.

Derivative

The term "derivative" or "derivatized" as used herein includes chemical modification of an agent. Illustrative of such chemical modifications would be replacement of hydrogen by a halo group, an alkyl group, an acyl group, or an amino group.

Chemical Modification

In one embodiment of the present technology, the agent may be a chemically modified agent. The chemical modification of an agent of the present technology may either enhance or reduce hydrogen bonding interaction, charge interaction, hydrophobic interaction, Van Der Waals interaction, or dipole interaction between the agent and the target. In some embodiments, the identified agent may act as a model (for example, a template) for the development of other compounds.

Although the disclosure herein refers to certain illustrated embodiments, it is to be understood that these embodiments are presented by way of example and not by way of limitation.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A formulation comprising a lipid composition comprising acylglycerol molecules of the following structure:

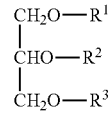

wherein R1, R2 and R3 are fatty acid moieties or —H such that said acylglycerol molecules comprise at least 20% w/w of at least one non-methylene-interrupted fatty acid moiety and at least 1% w/w of a second bioactive lipid moiety at one of positions R1, R2 and R3, said lipid composition formulated with a carrier for oral or topical administration wherein said carrier is not naturally associated with the acylglycerol molecules.

2. The formulation of claim 1, wherein said non-methylene-interrupted fatty acid moiety is selected from the group consisting of a 5,11,14-eicosatrienoic acid moiety, a 5,9,12-cis-octadecatrienoic acid moiety; and a 5,11,14,17-eicosatetraenoic acid moiety and combinations thereof.

3. The formulation of claim 1, wherein said second bioactive lipid moiety is selected from the group consisting of an omega-3 fatty acid moiety, a non-beta-oxidizable fatty acid moiety, a conjugated linoleic acid moiety and combinations thereof.

4. The formulation of claim 3, wherein said omega-3 fatty acid moiety is selected from the group consisting of an all-cis-5,8,11,14,17-eicosapentaenoic acid moiety, an all-cis-7,10,13,16,19-docosapentaenoic acid moiety, and an all-cis-4,7,10,13,16,19-docosahexaenoic acid moiety and combinations thereof.

5. The formulation of claim 3, wherein said non-beta-oxidizable fatty acid moiety is selected from the group consisting of a tetradecylthioacetic acid (TTA) moiety and a tetradecylselenoacetic acid (TSA) moiety and combinations thereof.

6. The formulation of claim 3, wherein said conjugated linoleic acid moiety is selected from the group consisting of a c9,t11 conjugated linoleic acid moiety, a t10,c12 conjugated linoleic acid moiety, a t9,t11 conjugated linoleic acid moiety, a t10,t12 conjugated linoleic acid moiety and combinations thereof.

7. The formulation of claim 1, wherein said formulation comprises at least 10% of said second bioactive lipid moiety.

8. The formulation of claim 1, further comprising at least one pharmaceutically acceptable carrier.

9. The formulation of claim 1, wherein said formulation is selected from the group consisting of an oil, tablet, capsule, powder, crystal, wax, emulsion, micelle, vesicle, or film.

* * * * *